(12) United States Patent
Santiago

(10) Patent No.: US 12,190,577 B2
(45) Date of Patent: Jan. 7, 2025

(54) METHODS AND SYSTEMS FOR PROVIDING HEALTH INTERACTION INFORMATION IN AN AUGMENTED REALITY PRESENTATION

(71) Applicant: CVS Pharmacy, Inc., Woonsocket, RI (US)

(72) Inventor: Eduardo Hernandez Santiago, Palm Coast, FL (US)

(73) Assignee: CVS Pharmacy, Inc., Woonsocket, RI (US)

(*) Notice: Subject to any disclaimer, the term of this patent is extended or adjusted under 35 U.S.C. 154(b) by 230 days.

(21) Appl. No.: 17/501,744

(22) Filed: Oct. 14, 2021

(65) Prior Publication Data
US 2023/0119707 A1   Apr. 20, 2023

(51) Int. Cl.
| | |
|---|---|
| *G06V 20/20* | (2022.01) |
| *G06F 21/31* | (2013.01) |
| *G06T 11/00* | (2006.01) |
| *G06T 19/00* | (2011.01) |
| *G16H 10/60* | (2018.01) |
| *G16H 70/40* | (2018.01) |
| *G06V 20/68* | (2022.01) |
| *G06V 30/19* | (2022.01) |

(52) U.S. Cl.
CPC .............. *G06V 20/20* (2022.01); *G06F 21/31* (2013.01); *G06T 11/00* (2013.01); *G06T 19/006* (2013.01); *G16H 10/60* (2018.01); *G16H 70/40* (2018.01); *G06V 20/68* (2022.01); *G06V 30/19153* (2022.01)

(58) Field of Classification Search
CPC ....... G06H 10/60; G06T 11/00; G06T 19/006; G06V 20/20; G06V 20/68
See application file for complete search history.

(56) References Cited

U.S. PATENT DOCUMENTS

| | | | |
|---|---|---|---|
| 6,588,670 B2 | 7/2003 | Bukowski | |
| 6,877,658 B2 | 4/2005 | Raistrick et al. | |
| 9,808,403 B2 | 11/2017 | Panzini et al. | |
| 10,552,575 B1 | 2/2020 | Mohebbi et al. | |

(Continued)

OTHER PUBLICATIONS

"Ways to Use Smartphone-Based Barcode Scanning in the Pharmacy," Scandit, Sep. 15, 2020, retrieved from https://www.scandit.com/blog/pharmacy-apps/, 7 pages.

*Primary Examiner* — Diane M Wills
(74) *Attorney, Agent, or Firm* — Sheridan Ross P.C.

(57) ABSTRACT

An interaction checking method, device, and system determines health interactions, in real time, as images are collected from an environment and provides augmented informational data presentations of the same. The interactions are based on health information, historical information, and stored interaction data. In particular, the images are received from a camera viewing the environment and an identity is determined of the objects in the environment. Based on the identity determined, information about the objects is retrieved from a memory device, and an interaction warning is determined for a specific combination of the objects if the objects were to be used together. A display device augments visual data of the environment with the information about the objects in a presentation to a user that includes the interaction warning and information about the objects.

20 Claims, 9 Drawing Sheets

(56) References Cited

U.S. PATENT DOCUMENTS

| | | | |
|---|---|---|---|
| 10,896,244 B2 | 1/2021 | Mohebbi et al. | |
| 2001/0001144 A1 | 5/2001 | Kapp | |
| 2006/0155542 A1 | 7/2006 | Vimegnon et al. | |
| 2008/0030309 A1 | 2/2008 | Darrouzet | |
| 2009/0254374 A1 | 10/2009 | Martinez et al. | |
| 2015/0234188 A1* | 8/2015 | Lee | G02C 7/085 345/633 |
| 2017/0061631 A1* | 3/2017 | Karasudani | G06T 1/0007 |
| 2017/0091424 A1* | 3/2017 | Haigh | H04L 63/08 |
| 2017/0161457 A1* | 6/2017 | Meredith | G16H 40/67 |
| 2018/0301209 A1* | 10/2018 | Kim | G16H 20/10 |
| 2019/0392955 A1 | 12/2019 | Israeli | |
| 2020/0013515 A1 | 1/2020 | Colister et al. | |
| 2020/0135331 A1* | 4/2020 | Mohebbi | G16H 70/20 |
| 2020/0334731 A1* | 10/2020 | Abdollahian | G06Q 30/0629 |
| 2020/0402673 A1 | 12/2020 | Oesterheld et al. | |
| 2021/0020287 A1 | 1/2021 | Pattanaik et al. | |
| 2021/0057070 A1* | 2/2021 | Ferguson, III | G06V 40/165 |
| 2021/0272533 A1* | 9/2021 | Croxford | G09G 5/003 |
| 2022/0351433 A1* | 11/2022 | King | G06V 10/82 |

\* cited by examiner

METHODS AND SYSTEMS FOR PROVIDING HEALTH INTERACTION INFORMATION IN AN AUGMENTED REALITY PRESENTATION

BACKGROUND

The present disclosure is generally directed to the display of health interaction information, in particular, toward the augmented reality presentation of drug interaction information.

Drug interactions are generally described as side effects, or altered actions, of a drug when mixed with specific medications or foods. In some cases, drug interactions can decrease the efficacy of a particular drug, increase the risks associated with taking a particular drug, and even negatively affect a drug user's health.

When a user is prescribed a drug, the user may be made aware of known interactions by a medical practitioner. However, when a user takes a mix of prescribed drugs and/or unprescribed drugs, tracking drug interactions becomes cumbersome and difficult resulting in potential gaps in the user understanding the associated drug interactions. These gaps can inadvertently cause the user to suffer from negative side effects due to unknown drug interactions.

BRIEF SUMMARY

It is with respect to the above issues and other problems that the examples presented herein were contemplated.

In one aspect, a mobile device includes a camera; a display device; a processor coupled to the camera and the display device; and a memory coupled with and readable by the processor and storing therein instructions that, when executed by the processor, cause the processor to: receive, from the camera, images of an environment; determine, from the images of the environment received, an identity of at least two objects in the environment, wherein the at least two objects correspond to at least one of a food, a medication, and a vitamin; retrieve, from a memory device based on the identity of the at least two objects in the environment, information about the at least two objects; determine, based on the information about the at least two objects, that an interaction warning is associated with a combination of the at least two objects used together; and present, by the display device as the images of the environment are received, the interaction warning.

Examples may include one of the following features, or any combination thereof. Aspects of the above mobile device include wherein the instructions further cause the processor to: present, by the display device as the images of the environment are received from the camera, the information about at least one object of the at least two objects when the at least one object appears in the images of the environment. Aspects of the above mobile device include wherein the mobile device comprises a head mounted display, and wherein presenting the information and the interaction warning comprises projecting light comprising the information and the interaction warning directly onto a retina of a user of the head mounted display. Aspects of the above mobile device include wherein the display device comprises a display screen, and wherein presenting the information and the interaction warning comprises rendering the images of the environment to the display screen as the images of the environment are received and rendering images of the information and the interaction warning in an augmented reality combined presentation. Aspects of the above mobile device include wherein the instructions further cause the processor to: authenticate a user of the mobile device; and retrieve, from a user account database in response to authenticating the user, heath information associated with the user, wherein the health information comprises at least one medical treatment, prescribed medication, preexisting condition, and state of health associated with the user. Aspects of the above mobile device include wherein the health information comprises a vision disability as the preexisting condition, and wherein presenting the information about each object when each object appears in the images of the environment further comprises at least one of adjusting a contrast, a color, and a size of the information presented based on the vision disability. Aspects of the above mobile device include wherein the instructions further cause the processor to: determine, based on the information about the at least two objects and the health information, that an interaction between at least one object of the at least two objects and a portion of the health information associated with the user comprises a personal health hazard to the user. Aspects of the above mobile device include wherein the instructions further cause the processor to: present, by the display device as the images of the environment are received from the camera, a health hazard warning comprising information about the interaction when the at least one object of the at least two objects appears in the images of the environment. Aspects of the above mobile device include wherein the instructions further cause the processor to: determine, as part of determining the identity of the at least two objects, an identity of a first object of the at least two objects at a first time; and determine, as part of determining the identity of the at least two objects, an identity of a second object of the at least two objects at a second time subsequent to the first time, and wherein the interaction warning is presented by the display device only when the second object of the at least two objects appears in the images of the environment. Aspects of the above mobile device include wherein the instructions further cause the processor to output audio, via a speaker of the mobile device, comprising the information about each object when each object appears in the images of the environment. Aspects of the above mobile device include wherein the instructions further cause the processor to output a vibration, via a tactile transducer of the mobile device, upon determining the identity of the at least two objects in the environment.

In another aspect, a method includes receiving, from at least one camera of a mobile device, digital images of an object; determining, based on the digital images received, an identity of the object; retrieving, based on the identity, information about the object; determining an authentication of a user of the mobile device with a user health account; presenting, by a display device of the mobile device when the user is determined to be unauthenticated with the user health account, the information about the object while the object remains visible in the digital images as the digital images are received from the at least one camera; retrieving, from the user account, health information for the user only when the user is determined to be authenticated with the user health account; determining whether an interaction between the object and a portion of the health information for the user comprises a health hazard to the user; and presenting, by the display device when the interaction between the object and the portion of the health information for the user is determined to comprise the health hazard to the user, an interaction warning describing the interaction while the object remains visible in the digital images.

Examples may include one of the following features, or any combination thereof. Aspects of the above method include wherein the interaction warning is presented as the digital images are received from the at least one camera. Aspects of the above method include wherein at least one of the information about the object and the interaction warning are rendered via the display device as an augmented reality presentation, and wherein the at least one of the information about the object and the interaction warning are overlaid upon the images received from the at least one camera, in real time, as the digital images are received from the at least one camera. Aspects of the above method include wherein the object is at least one of a food, a medication, and a vitamin. Aspects of the above method include wherein the health information for the user comprises at least one medical treatment, prescribed medication, preexisting condition, and state of health of the user. Aspects of the above method include wherein the heath information comprises a vision impairment as the preexisting condition, and wherein presenting the information about the object while the object remains visible in the digital images further comprises at least one of adjusting a contrast, a color, a filter of light, and a size of the information presented based on the vision impairment.

In yet another aspect, a non-transitory computer-readable medium includes instructions stored therein that, when executed by a processor, cause the processor to: receive, from a camera, video images of an environment; determine, from the video images received, an identity of at least two objects in the environment, wherein the at least two objects correspond to at least one of a food, a medication, and a vitamin; retrieve, from a memory device based on the identity of the at least two objects in the environment, information about the at least two objects, wherein at least a portion of the information about the at least two objects is not visible on the at least two objects; determine, based on the information about the at least two objects, that an interaction warning is associated with combining the at least two objects together; and present, by a display device as the video images of the environment are received, the interaction warning.

Examples may include one of the following features, or any combination thereof. Aspects of the above computer-readable medium include wherein determining the identity of the at least two objects in the environment comprises at least one of visual recognition and optical character recognition of the at least two objects using artificial intelligence enabled by a machine learning engine analyzing the video images. Aspects of the above computer-readable medium include wherein retrieving the information about the at least two objects comprises accessing a database comprising identities of objects and corresponding known interactions, ingredients, and names, and wherein the database comprises the identity of the at least two objects.

The preceding is a simplified summary of the disclosure to provide an understanding of some aspects of the disclosure. This summary is neither an extensive nor exhaustive overview of the disclosure and its various aspects, examples, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, examples, and configurations of the disclosure are possible utilizing, alone or in combination, one or more of the features set forth above or described in detail below. All examples and features mentioned above can be combined in any technically possible way.

Numerous additional features and advantages are described herein and will be apparent to those skilled in the art upon consideration of the following Detailed Description and in view of the figures.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, examples, and configurations of the disclosure, as illustrated by the drawings referenced below.

DETAILED DESCRIPTION

Figure 1:
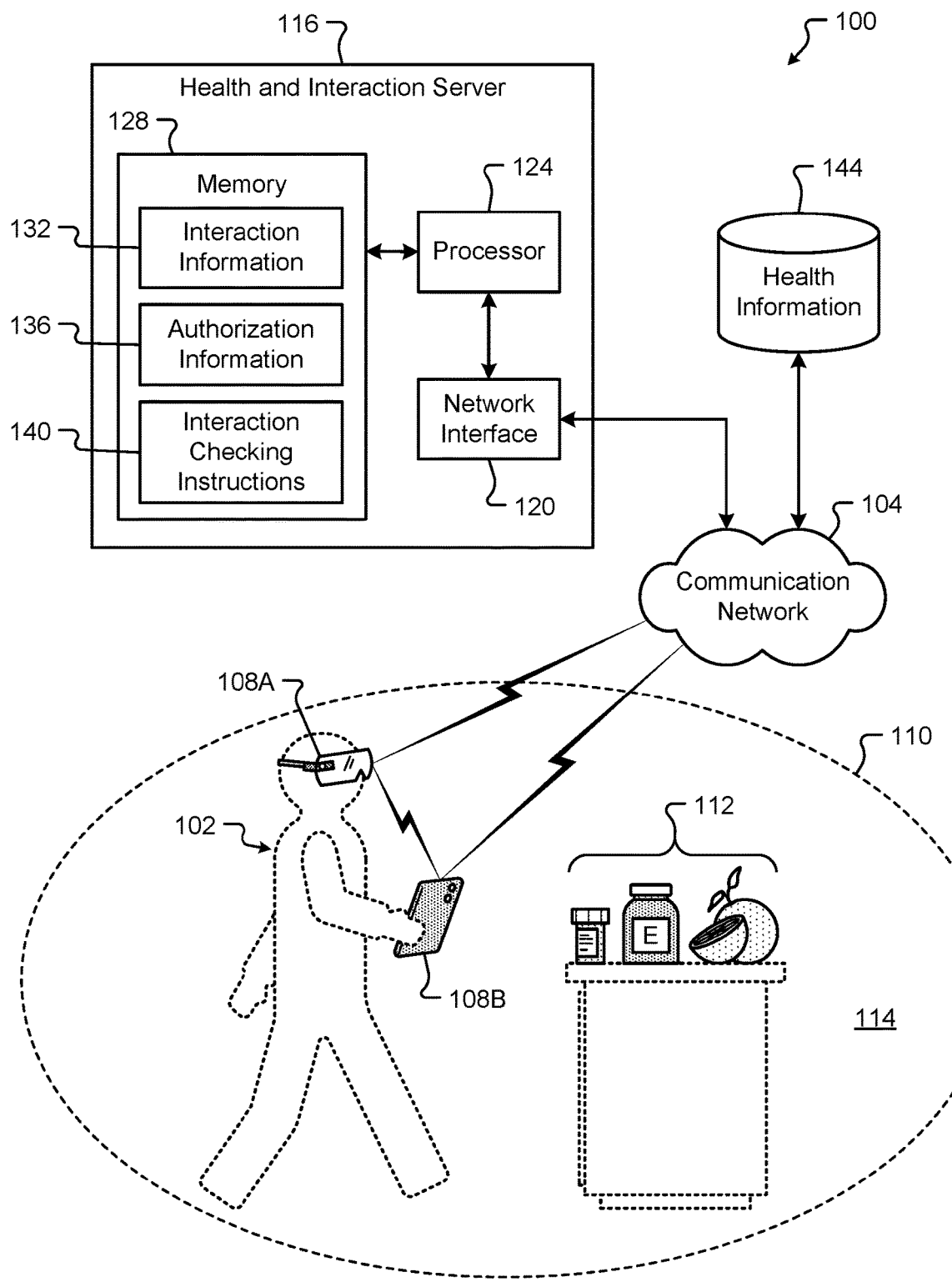
FIG. 1 is a block diagram of a health interaction checking system in accordance with examples of the present disclosure.

Before any examples of the disclosure are explained in detail, it is to be understood that the disclosure is not limited in its application to the details of construction and the arrangement of components set forth in the following description or illustrated in the drawings. The disclosure is capable of other examples and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The ensuing description provides examples only, and is not intended to limit the scope, applicability, or configuration of the claims. Rather, the ensuing description will provide those skilled in the art with an enabling description for implementing the described examples. It being understood that various changes may be made in the function and arrangement of elements without departing from the spirit and scope of the appended claims.

Various aspects of the present disclosure will be described herein with reference to drawings that may be schematic illustrations of idealized configurations.

An augmented reality (AR), and/or mixed reality (MR), drug interaction checker helps solve the problem of a possible unknown drug interaction for a user. For example, a smartphone/tablet or head-mounted display (HMD) device of a user may employ a camera to pick up and identify a drug or vitamin along with another drug or vitamin and overlay rich visual/audio information informing the user of possible drug interactions. The experience can happen in an unauthenticated state (e.g., a guest state) in which the user would be able to scan any drug/vitamin, etc. or if they are authenticated (e.g., signed in) the user would be able to get additional information about other possible drug interactions with medications/vitamins found in the user's health data account. In some cases, haptic feedback may be used to indicate to a user that a successful scan has been made, regardless of the abilities of the user.

By using the drug interaction checker, the user is provided with rich visual and/or audio information about possible drug interactions. This visual information is contextual to each drug/vitamin and may include automatically adjusting a contrast, a color, and a size of the information from what appears on a prescription paper, drug/vitamin label, and/or a mobile device screen in typical formatting. When the user has a vision disability, the font size may be increased, the user may be provided with enhanced contrast control, and/or be provided with audio feedback and/or output. At least one advantage of this approach includes providing those with vision disabilities the ability to navigate what medications they have and what medications might interact with other medications/vitamins in their medicine cabinet. Further benefits of the drug and health interaction methods and systems described herein include, but are in no way limited to, minimizing the amount of work required of users by looking up known drug interactions, typing long drug names into an online drug interaction checker, preventing data entry errors associated with the same, and automatically tracking and adding information to a user's personal health account for ensuring existing and/or future drug interactions are conveyed to a user in the best mode possible.

Referring initially to FIG. 1, a block diagram of a health interaction checking system 100 is shown in accordance with examples of the present disclosure. The health interaction checking system 100 may include at least one mobile device 108A, 108B of a user 102 in an environment 114. One or more objects 112 may be disposed in the environment 114 of the user 102. The objects 112 may correspond to at least one of a food (e.g., a beverage, a consumable, a meal or a portion thereof, etc.), a vitamin, a medication (e.g., a prescribed drug, an over-the-counter (OTC) drug, a medicine, a topical, etc.). Each of the mobile devices 108A, 108B may independently, or in communication with one another, communicate over a communication network 104 to a health and interaction server 116 and/or a health information memory 144 (e.g., computer-readable memory storage device, etc.).

The communication network 104 may comprise any type of known communication medium or collection of communication media and may use any type of protocols to transport messages between endpoints (e.g., the mobile devices 108A, 108B, the health and interaction server 116, etc.). The communication network 104 may include wired and/or wireless communication technologies. The Internet is an example of the communication network 104 that constitutes an Internet Protocol ("IP") network consisting of many computers, computing networks, and other communication devices located all over the world, which are connected through many telephone systems and other means. Other examples of the communication network 104 include, without limitation, a standard Plain Old Telephone System ("POTS"), an Integrated Services Digital Network ("ISDN"), the Public Switched Telephone Network ("PSTN"), a Local Area Network ("LAN"), a Wide Area Network ("WAN"), a VoIP network, a cellular network, and any other type of packet-switched or circuit-switched network known in the art. In addition, it can be appreciated that the communication network 104 need not be limited to any one network type, and instead may be comprised of a number of different networks and/or network types. The communication network 104 may comprise a number of different communication media such as coaxial cable, copper cable/wire, fiber-optic cable, antennas for transmitting/receiving wireless messages, optical/infrared, and combinations thereof.

The mobile devices 108A, 108B may correspond to any mobile communication device or mobile computer (e.g., smartphone, tablet, personal computer, etc.) that is capable of scanning objects 112 in an environment 114 (e.g., with a camera, etc.), determining an identity of the objects 112, and determining whether any health interaction exists for a specific combination of the objects 112. Although a user 102 is depicted in FIG. 1 as having multiple mobile devices 108A, 108B, only one mobile device 108A, 108B is needed to enable and/or execute the methods described herein. The head-mounted device 108A may correspond to an AR display device, an MR display device, and/or some other HMD device. Examples of the head-mounted device 108A may include, but are in no way limited to, Google™ Glass, Oculus Rift® virtual reality (VR) HMD device, Samsung® Odyssey+ VR headset, and/or the like. As can be appreciated, the head-mounted device 108A may generate augmented presentations in AR, MR, and/or VR. These augmented presentations may be rendered by a display screen of the head-mounted device 108A or projected directly onto a retina of the user 102. The mobile communication device 108B may correspond to a smartphone, a tablet, a laptop, a personal computer, or the like. The mobile communication device 108B may include at least one display screen that is capable of rendering images of the environment 114 and information overlaid with the images of the environment 114, for example, in an AR format. The mobile devices 108A, 108B may correspond to the mobile device 108 described in conjunction with FIG. 2, or vice versa. In any event, the mobile devices 108A, 108B may include one or more cameras (e.g., image sensors, etc.) that are capable of recording images of a portion of the environment 114 that is within a detection range 110 of the cameras.

As illustrated in FIG. 1, the objects 112 may include at least one medication, vitamin, and food. Although shown in containers, the medication and the vitamins may be identified by the mobile devices 108A, 108B outside of a container based on, for example, shape, color, and/or other identifiable markings (e.g., visible brand names, edible ink marking, two-dimensional codes, matrix codes, etc., and/or combinations thereof). As described herein, when the objects 112 are found within the detection range 110 of the camera of the head-mounted device 108A and/or the mobile communication device 108B, the objects 112 are identified. The identification is then used to determine known interactions. This determination may be done on the mobile device 108A, 108B alone, in the health and interaction server 116 alone, between the mobile device 108A, 108B and the health and interaction server 116 communicating with one another over the communication network 104, and/or on the mobile device 108A, 108B based on information retrieved from the health information memory 144 across the communication network 104. Once the determination is made, the user 102 may be presented with information about the objects 112. This information may include potential interactions, identification information, prescription information, and/or combinations thereof. The terms "drug interactions," "health interactions," or "interactions" and variations thereof may be used interchangeably herein to refer to any specific combination of the objects 112 and/or between at least one object 112 and health information for the user 102 that, when combined, used together, or mixed may result in an ailment, illness, side effect, or altered action of a drug, etc. Examples of the interactions may cause, among other things, a decrease in the efficacy of a particular drug, an increase in the risks associated with taking a particular drug, toxicity for a drug user, and/or an adverse health effect for a specific drug user.

The health and interaction server 116 is further shown to include a network interface 120, a processor 124, and a memory 128. These resources may enable functionality of the health and interaction server 116 as is described herein. For example, the network interface 120 provides the health and interaction server 116 with the ability to send and receive communication packets, or the like, over the communication network 104. The network interface 120 may be provided as a network interface card (NIC), a network port, a modem, drivers for the same, and the like. Communications between the components of the health and interaction server 116 and other devices connected to the communication network 104 may flow through the network interface 120.

The processor 124 may correspond to one or more computer processing devices. For example, the processor 124 may be provided as silicon, an Application-Specific Integrated Circuit (ASIC), as a Field Programmable Gate Array (FPGA), any other type of Integrated Circuit (IC) chip, a collection of IC chips, and/or the like. In some examples, the processor 124 may be provided as a Central Processing Unit (CPU), a microprocessor, or a plurality of microprocessors that are configured to execute the instructions sets stored in memory 128. Upon executing the instruction sets stored in memory 128, the processor 124 enables various communications, interaction checking and determinations, object identifications, authorization and access functions, and/or presentation functions of the mobile devices 108A, 108B, and may provide an ability to establish and maintain communication sessions between communication devices over the communication network 104 when specific predefined conditions are met. The processor 124 may be configured as a virtual processor(s) executing on one or more physical processors. The execution of a virtual processor may be distributed over a number of physical processors or one physical processor may execute one or more virtual processors. Virtual processors are presented to a process as a physical processor for the execution of the process while the specific underlying physical processor(s) may be dynamically allocated before or during the execution of the virtual processor wherein the instruction stack and pointer, register contents, and/or other values maintained by the virtual processor for the execution of the process are transferred to another physical processor(s). As a benefit, the physical processors may be added, removed, or reallocated without affecting the virtual processors execution of the processes. For example, the processor 124 may be one of a number of virtual processors executing on a number of physical processors (e.g., "cloud," "farm," array, etc.) and presented to the processes herein as a dedicated processor. Additionally or alternatively, the physical processor(s) may execute a virtual processor to provide an alternative instruction set as compared to the instruction set of the virtual processor (e.g., an "emulator"). As a benefit, a process compiled to run a processor having a first instruction set (e.g., Virtual Address Extension (VAX)) may be executed by a processor executing a second instruction set (e.g., Intel® 9xx chipset code) by executing a virtual processor having the first instruction set (e.g., VAX emulator).

The memory 128 may include any type of computer memory device or collection of computer memory devices. Non-limiting examples of the memory 128 include Random Access Memory (RAM), Read Only Memory (ROM), flash memory, Electronically-Erasable Programmable ROM (EEPROM), Dynamic RAM (DRAM), etc. The memory 128 may be configured to store the instruction sets depicted in addition to temporarily storing data for the processor 124 to execute various types of routines or functions. Although not depicted, the memory 128 may include instructions that enable the processor 124 to store data into a health information memory 144 and/or memory of a mobile device 108A, 108B and retrieve information from the health information memory 144 and memory of the mobile device 108A, 108B. Additionally or alternatively, the health information memory 144 or data stored therein may be stored internal to the server 116 (e.g., within the memory 128 of the server 116 rather than in a separate database or memory storage device).

The memory 128 may store various data and instruction sets that allow the health and interaction server 116 to provide interaction checking and authorization for mobile devices 108A, 108B in the health interaction checking system 100. Examples of this data may include, but are in no way limited to, interaction information 132 and authorization information 136. The interaction information 132 may comprise known interactions between objects 112 (e.g., foods, vitamins, medications, etc.), known interactions between objects 112 and certain health conditions (e.g., diseases, ailments, and/or other preexisting conditions, etc.), for example, that may be associated with a user 102, and/or known interactions between types of objects 112 (e.g., general or broad classifications of common objects such as "statins," "citrus juices," "fatty foods," etc.) and other objects 112, types of objects 112, health conditions, and/or types of health conditions (e.g., general or broad classifications of health conditions such as "depression," "hypertension," "pregnancy," etc.).

In some examples, health information associated with the user 102 may be stored in a secure memory location (e.g., of the memory 128 and/or the health information memory 144, etc.). For instance, the health information may be associated with a health account of a user 102 or user account. A user account database (e.g., stored in the health information memory 144) that is associated with the user account may include private details regarding a user's health, medical history, medical treatments received and/or scheduled, prescribed medications, nonprescribed medications taken, preexisting conditions, a general state of health for a user 102, and more. Since this information is not only private but is also sensitive to a user 102, the information may be restricted to unauthorized parties (e.g., unauthorized users, devices, etc.). Stated another way, the information associated with a user account may only be accessible by an authorized party. The authorization information 136 may store an identification, access credentials, and a registration status for a user 102 with a user account. A user 102 may request access of the user account from a mobile device 108A, 108B that is communicated to the health and interaction server 116 over the communication network 104. In response, the health and interaction server 116 may refer to information stored in the authorization information 136 and determine whether the user 102 is authorized to access the user account. In the event that the user 102 is authorized, the user 102 may operate the mobile device 108A, 108B in an authenticated, or "signed-in," state allowing the user 102 to scan objects 112 in the environment 114 and retrieve personal and private information (e.g., health information, etc.) from the user account. If not authorized, the user 102 may operate the mobile device 108A, 108B in an unauthenticated, or "guest," state still able to scan objects 112 in the environment 114 but without retrieving the personal and private information from the user account.

An illustrative instruction set that may be stored in the memory 128 may include, without limitation, an interaction checking instruction set 140. Functions of the server 116 enabled by this instruction set will be described further herein. It should be appreciated that the instruction set depicted in FIG. 1 may be combined (partially or completely) with other instruction sets or may be further separated into additional and different instruction sets, depending upon configuration preferences for the server 116. Stated another way, the particular instruction set depicted in FIG. 1 should not be construed as limiting examples described herein.

The interaction checking instruction set 140, when executed by the processor 124, may enable the health and interaction server 116 to identify objects 112, retrieve known interactions in the interaction information 132 and/or health information memory 144, determine interaction warnings that should be presented to a user 102 (e.g., via at least one mobile device 108A, 108B), cause the interactions to be rendered or projected by the mobile devices 108A, 108B, determine an authorization of a user 102 with a user account, retrieve information from the health information memory 144 and/or mobile devices 108A, 108B, and/or the like.

Figure 2:
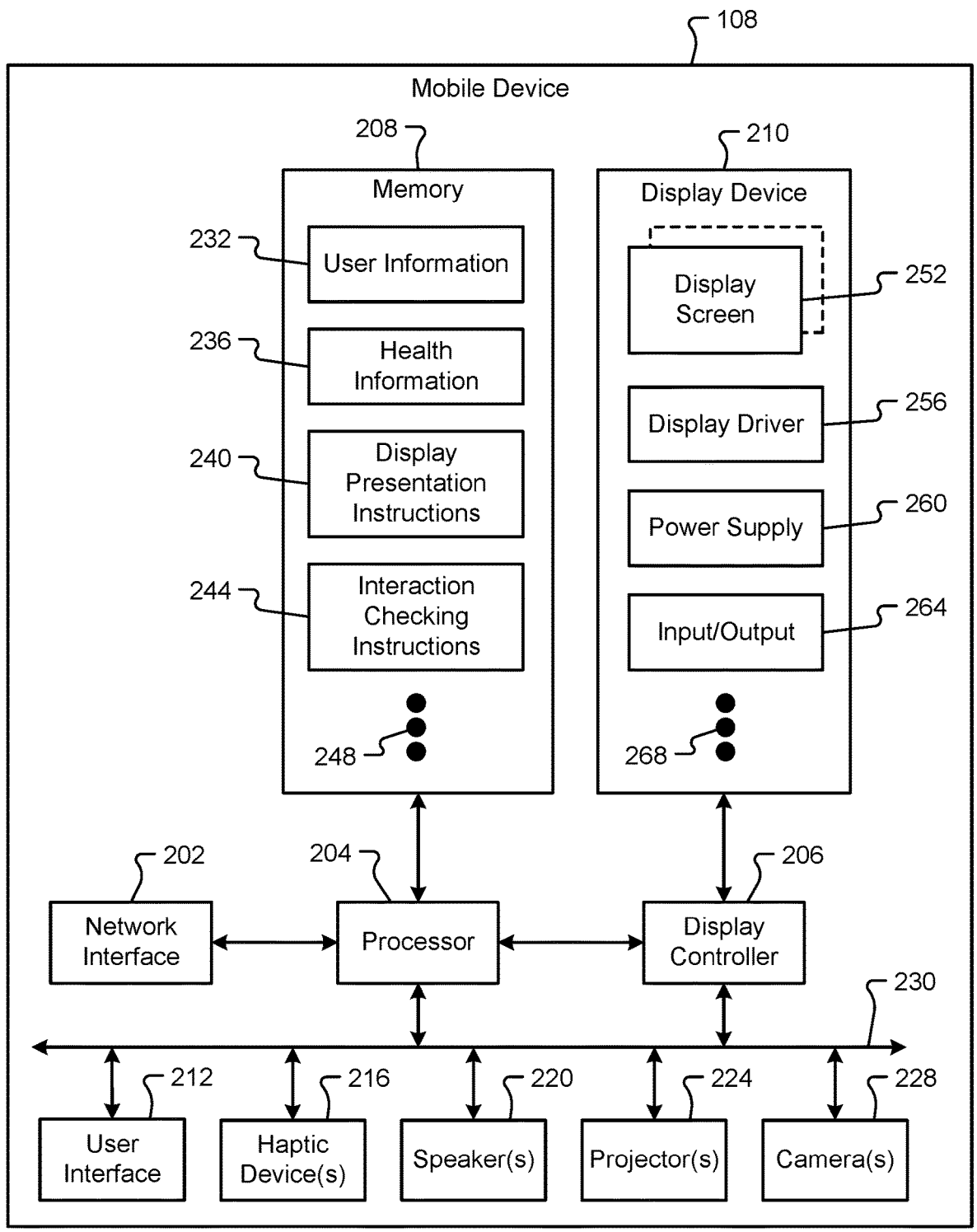
FIG. 2 is a block diagram depicting an illustrative mobile device that enables health interaction checking and augmented reality or mixed reality presentations.

FIG. 2 is a block diagram depicting an illustrative mobile device 108 that enables health interaction checking and the various AR or MR presentations described herein. The mobile device 108 may correspond to one or more of the mobile devices 108A, 108B described in conjunction with FIG. 1, or vice versa.

The mobile device 108 is depicted to include a network interface 202, a processor 204, a display controller 206, a memory 208, a display device 210, a user interface 212, and one or more haptic devices 216, speakers 220, projectors 224, and cameras 228. The components of the mobile device 108 may be interconnected with one another via power and/or communication bus 230. The network interface 202 may be similar, or identical, to the network interface 120. Examples of a suitable network interface 202 may include, without limitation, an Ethernet port, a universal serial bus (USB) port, a NIC, an antenna, a driver circuit, a modulator/demodulator, etc. In some examples, the processor 204 may be similar or identical to the processor 124. In other words, the processor 204 may correspond to one or many microprocessors, CPUs, microcontrollers, or the like. The processor 204 may be configured to execute one or more instruction sets stored in the memory 208.

The memory 208 may be similar, or identical, to the memory 128. For instance, the memory 208 may include one or multiple computer memory devices that are volatile or non-volatile. The memory 208 may be configured to store information and instruction sets that enable the user 102 to interact with the mobile device 108, that enable interaction checking operations, that enable augmented presentations of the environment 114 (and objects 112 in the environment 114) along with information about identified objects 112 in the environment 114, and that enable communications across the communication network 104 (e.g., with the health and interaction server 116, etc.). The information that may be stored in the memory 208 may include user information 232 and health information 236. The user information 232 may include identification information for the user 102 (e.g., name, username, number, etc.) that uniquely identifies the user 102. Additionally or alternatively, the user information 232 may include identification information for a user account of the user 102 of the mobile device 108. For example, the user information 232 may include an account number, username, registration status, password or key, and/or other authentication information for the user account. The health information 236 may comprise information for the user 102 of the mobile device 108. This health information 236 may include, without limitation, known interactions, previously identified objects 112, the medical history, medical treatments received, medical treatments scheduled, prescribed medications, nonprescribed medications taken, preexisting conditions, a general state of health for a user 102, and more. Examples of instruction sets that may be stored in the memory 208 may include a display presentation instruction set 240, an interaction checking instruction set 244, and/or other instruction sets 248.

The display presentation instructions 240, when executed by the processor 204, may enable the mobile device 108 to provide various display and/or auditory information presentations (e.g., render information to the display device 210 and/or project images via the projectors 224, play audio output via the speakers 220, etc.). The information may include interaction warnings, information, images, icons, audio alerts, spoken output, and presentations that are overlaid onto an image of the environment 114 viewed by the mobile device 108. In some examples, the display presentation instruction set 240 may cause the display device 210 to render images (e.g., video images) of the environment 114 and overlay additional information (e.g., interaction warnings, information about objects 112, etc.) to the display device 210 simultaneously with the images of the environment 114 rendered. In one example, the display presentation instruction set 240 may cause the projector 224 to project images (e.g., video images) of additional information (e.g., interaction warnings, information about objects 112, etc.) directly onto a retina of a user 102 viewing the environment 114 through a clear lens, or set of glasses, of a head-mounted device 108A. Although, in this example, the head-mounted device 108A may not render the environment 114 or objects 112, the additional information may be projected onto the retina of the user 102 to appear as if the information is overlaid onto the environment 114 and/or objects 112 that is visible through the clear lens. In yet another example, the head-mounted device 108A may correspond to a VR headset that generates simulated images of the objects 112, the environment 114, and the additional information to a display device 210. In any of the examples described above, this overlay of additional information may be referred to herein as an augmented information presentation, augmented presentation, or AR combined presentation.

The interaction checking instruction set 244 may be similar, or identical, to the 140. The interaction checking instruction set 244, when executed by the processor 204, may enable the mobile device 108 to identify objects 112 in the environment 114, determine interactions, determine interaction warnings, and cause the display device 210 or the projectors 224 to provide the augmented presentation. In one example, the mobile device 108 may operate independently of the health and interaction server 116. In this case, the interaction checking instruction set 244 may refer to health information 236 stored in the health information 236 and/or communicate across the communication network 104 to the health information memory 144. In some examples, the mobile device 108 may operate with the health and interaction server 116. For instance, when a user 102 is registered with a user account, the mobile device 108 may communicate with the health and interaction server 116 to retrieve user account information that is stored in a user account database. As provided above, the user account database may include health information that is associated with the user and that is stored in a secure memory location (e.g., of the health information memory 144, etc.).

The mobile device 108 may include one or more display devices 210 configured to render information, real-time video, windows, pop-ups, warning, environmental information, interactive elements, and/or other visual output to one or more display screens 252. The mobile device 108 may include one or more display controllers 206 configured to control an operation of the display device 210. This operation may include the control of input (e.g., user input via the user interface 212, command input via the instruction sets in memory 208, combinations thereof, etc.), output (e.g., display, rendered images, augmented information presentations, etc.) and/or other functions of the display device 210.

The display device 210 may one or more display screens 252 that are configured to selectively activate pixels and/or display elements to render one or more windows, icons, interactive elements, warnings, characters, images, colors, etc. Examples of the display screen 252 may include, without limitation, a liquid crystal display (LCD), a light-emitting diode (LED) display, an electroluminescent display (ELD), an organic LED (OLED) display, and/or some other two-dimensional and/or three-dimensional display. The one or more display screens 252 may be separated into a left display and a right display. In a VR head-mounted device 108A, the left display may correspond to a display arranged adjacent a left eye of a user 102 and the right display may correspond to a display arranged adjacent a right eye of the user 102. The display device 210 may render information in one or more areas (e.g., windows, pop-ups, points adjacent objects 112, etc.) that are superimposed over images of objects 112 in the environment 114 rendered of the display screen 252.

The display device 210 may include a display driver 256, a power supply 260, an input/output 264, and/or other components 268 configured to enable operation of the display device 210. The display driver 256 may receive commands and/or other data provided by the processor 204 and one or more of the instruction sets in memory 208. In response to receiving the commands, the display driver 256 may be configured to generate the driving signals necessary to render the appropriate images to the display screen 252. The power supply 260 may provide electric power to the components of the display device 210. In some examples, the power supply 260 may include a transformer and/or other electronics that prevent overloading, condition power signals, and/or provide backup power to the display device 210. The input/output 264 may correspond to one or more connections for receiving or exchanging information and/or video from components of the mobile device 108. The input/output 264 may include an interconnection to the network interface 202. For example, the input/output 264 may include a high-definition multimedia interface (HDMI) input, composite video, component video, H.264, or other video connection.

The user interface 212 may correspond to any input type of input and/or output device that enables the user 102 to interact with the mobile device 108. The nature of the user interface 212 may depend on the type of the mobile device 108. For example, if the mobile device 108 is configured as a head-mounted device 108A, the user interface 212 may comprise a speaker, eye-tracking camera, side button, or other touch input device, or the like. As another example, if the mobile device 108 is configured as a mobile communication device 108B, the user interface 212 may include, without limitation, one or more touch-sensitive displays, LED/LCD display screens, buttons, switches, etc. Other examples of the user interface 212 may include, without limitation, a touchscreen, keyboard, microphone, mouse, button, switch, or other component of the mobile device 108 that is capable of receiving input from the user 102.

The haptic devices 216 may include one or more devices that are capable of providing a touch-based output via the mobile device 108. The haptic devices 216 may provide a haptic feedback for a user 102 that is interacting with, or using, the mobile device 108. For example, when a user 102 successfully scans at least one of the objects 112, the haptic devices 216 may provide a vibration indicating the successful scan. Other examples may include providing the haptic feedback when an interaction warning is presented, when at least one of the objects 112 is identified, and/or at some other device interaction between the user 102 and the mobile device 108. The haptic devices 216 may correspond to a coin vibration motor, an eccentric rotating mass vibration motor, a haptic vibration motor, a linear resonant actuator, and/or some other motor that produces an oscillating or vibrating force. This force may be transmitted through a body of the mobile device 108 to the user 102 wearing or using the mobile device 108.

The mobile device 108 may include one or more speakers 220 disposed in, or on, the mobile device 108. The speakers 220 may provide an audio output of the mobile device 108 in monaural form and/or stereophonic sound. The speakers 220 may comprise at least one dynamic loudspeaker, electroacoustic transducer, electrostatic speaker, tactile sound transducer, moving-coil loudspeaker, subwoofer, or other speaker.

Depending on the configuration of the mobile device 108, one or more projectors 224 may be included that are capable of projecting visual information directly onto the retina of the eye of a user 102. These projectors 224 may utilize a projection element and waveguide to direct images generated by the mobile device 108 into the retina of the user 102. Examples of the projectors 224 may include, but are in no way limited to, transmissive display panels, a near eye display (NED), a digital light projection (DLP) display, and/or other image projector with associated optics. When configured as an AR-type of head-mounted device 108A, the mobile device 108 may comprise the projectors 224 described above.

The mobile device 108 may include at least one camera 228, or image capture device (e.g., image sensor), that is configured to capture still and/or video images in proximity to the mobile device 108 (e.g., in the detection range 110 of the camera 228). The camera 228 may include, or be associated, with additional devices, such as light sources, flashes, infrared emitters, etc., to provide a clear image capture environment. As provided herein the camera 228 may be controlled by the processor 204 in conjunction with signals from the interaction checking instructions set 244 and/or other instruction sets stored in the memory 208. In some examples, the mobile device 108 may include at least two cameras 228 that are capable of generating stereo images of the environment 114 including objects 112 in the environment 114.

Figure 3:
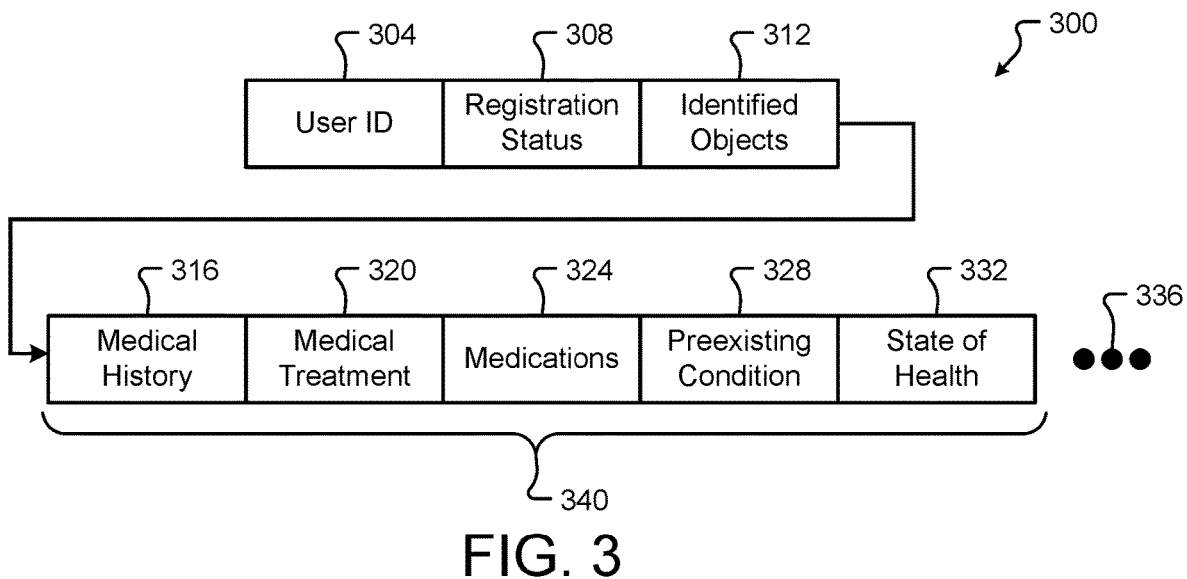
FIG. 3 is a block diagram depicting a health information data structure stored in a user information memory location for maintaining health information about the user of the mobile device.

Referring now to FIG. 3, a block diagram of a health information data structure 300 is shown storing health information about, or associated with, a user 102. The health information data structure 300 may be maintained as part of the user information 232 and/or as a part of the user account database stored in the health information memory 144. In some examples, the health information memory 144 may comprise different unique memory locations for each user registered with a user account (e.g., on the health and interaction server 116, etc.). As a non-limiting example, the health information data structure 300 may be used to store user information, user account information, tracked data, and health information. Even more specifically, the health information data structure 300 may include a plurality of data fields that include, for instance, a user identification field 304, a registration status field 308, an identified objects field 312, a medical history field 316, a medical treatment field 320, a medications field 324, a state of health field 332, and/or other fields 336. In some examples, field 316 through field 332 of the health information data structure 300 may be referred to herein as health information 340.

The user identification field 304 may be used to store any type of information that uniquely identifies a user 102. In some examples, the user identification field 304 may store one or more of a name, character, identification number, and/or username for a user 102. The user identification field 304 may include user account information for the user 102. This user account information may be associated with a health account for the user, where the user is registered. The user identification field 304 may include access credentials, passwords, keys, or partial keys that are used to authenticate a user 102 with a user account.

The registration status field 308 may be used to store data describing a registration status of the user 102 with a user account. In some examples, the user 102 may be registered with one or more user accounts. The user accounts may be hosted and/or maintained by different entities. While a user 102 may be registered with one user account, the same user 102 may not be registered with others. The registration status field 308 may indicate whether a user 102 is registered with a particular user account.

The identified objects field 312 may be used to store data of objects 112 previously identified and associated with the user 102 of the mobile device 108. For instance, as the user 102 scans objects 112 in the environment 114, or as the cameras 228 detect objects 112 in the environment 114, and the objects 112 are identified, the identified objects field 312 may be used to maintain (e.g., track, record, etc.) a list of each identified object. When making interaction determinations, the interaction checking instructions 140, 244 may retrieve data stored in the identified objects field 312. In some cases, this retrieval may pick up information that is not otherwise stored in the health information 340 and/or elsewhere associated with the user 102. Moreover, by maintaining historical information about previously identified objects, the mobile device 108 may present "potential" interaction warnings indicating that the user 102 may be at risk if a later-detected object of the objects 112 interacts with one or more of the previously identified objects. This time-independent approach allows the health interaction checking system 100 to provide augmented information presentations and warnings even when two objects 112 that could result in an interaction are not found in the environment 114 at the same time.

The medical history field 316 may be used to store past medical claims made by a user 102. The medical claims may be associated with a user account. In some examples, the medical claims may be stored in the health information memory 144 and may be managed by the health and interaction server 116. The medical claims may include information such as medical costs incurred and/or treatments received for medical services rendered to the user 102. These medical claims may be coded to identify each service and may provide a historical medical profile of the user 102. Interactions may be determined by extracting data from the medical history field 316 (e.g., via the interaction checking instructions 140, 244) and comparing the data to known interactions stored in the health information memory 144 and/or the health information 236.

The medical treatment field 320 may be used to store data about medical treatments associated with the user 102. These treatments may include, but are in no way limited to, therapies, dosage regimen, self-treatments, and/or other present and/or future treatments associated with the user 102. In some examples, the interaction checking instructions 140, 244 may access the data in the medical treatment field 320 to determine when an interaction may exist for a user 102. By way of example, a user 102 may be engaging in a first treatment at a first time and a second treatment at a second time. In this example, there may be no interaction for one or more objects 112 identified at the first time, but there may be an interaction for objects 112 at the second time. In this case, the interaction checking instructions 140, 244 (in conjunction with the display presentation instructions 240), may cause augmented interaction information to be presented to the user 102 (e.g., via the display device 210 or the projectors 224) that while there is no immediate interaction, a future interaction is possible at the second time. Among other things, this information allows a user 102 to plan for potential interactions based on information that may otherwise be forgotten or too difficult to track.

The medications field 324 may be used to store data about prescribed medications, unprescribed medications, and/or other drugs that have been associated with the user 102. Prescribed medications may include any medications that have been prescribed by a medical practitioner for the user 102 at any time. The unprescribed medications may include OTC medications the user 102 is taking, or that have been observed (e.g., by the cameras 228 of the mobile device 108) in the environment 114. This information may be stored in the user account database of the user account for the user 102. In one example, the information may form at least a portion of the medical file of the user 102.

The preexisting condition field 328 may be used to store diagnosis data for the user 102 that is associated with one or more identified health conditions. Examples of these health conditions may include, but are in no way limited to, asthma, depression, diabetes, hemophilia, hypertension, gastrointestinal (GI) toxicity, hepatobiliary dysfunction, immunodeficiency, pregnancy, vision impairment (e.g., legal blindness, astigmatism, near/far-sightedness, color blindness, etc.), and/or other preexisting conditions of the user 102. The interactions described herein may be based not only on known interactions between objects 112, but may also be based on at least one of the objects 112 and a preexisting condition that is known for the user 102. As can be appreciated, the interaction checking instructions 140, 244 may use data in the preexisting condition field 328 of the health information data structure 300 when making interaction determinations.

The state of health field 332 may be used to store data corresponding to an overall state of health of the user 102. For instance, the user 102 may be determined to be athletic, underweight, obese, or morbidly obese. This information may be stored in the state of health field 332. Additionally or alternatively, the state of health field 332 may be used to store a body mass index (BMI), a fat percentage, water percentage, data from a fitness tracker (e.g., a smart watch or other wearable fitness tracker), and/or other health indicator. The interaction checking instructions 140, 244 may use data in the state of health field 332 of the health information data structure 300 when making interaction determinations and determining risk levels for a user 102.

Figure 4:
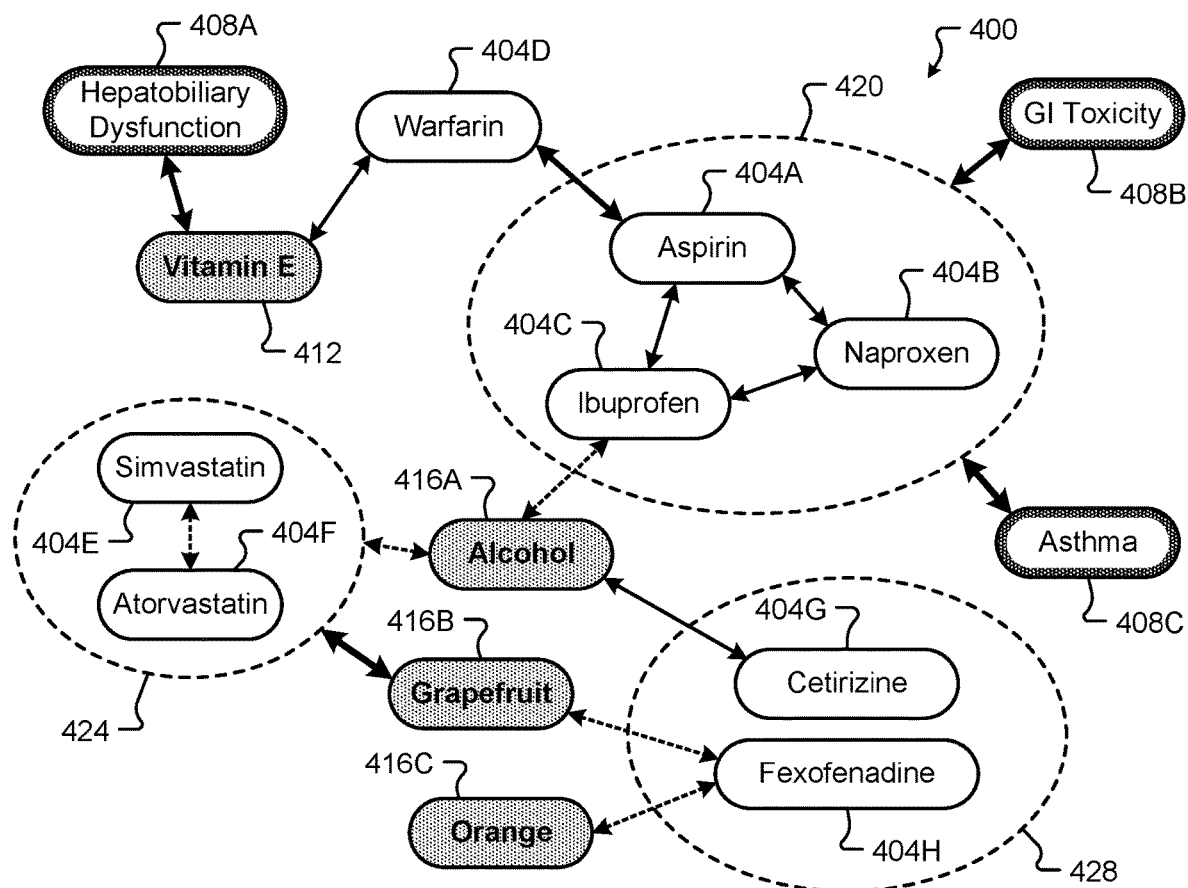
FIG. 4 is a schematic representation of a node-link diagram used in maintaining and updating health interactions in accordance with examples of the present disclosure.

FIG. 4 shows a schematic representation of a node-link diagram 400 used in maintaining and updating health interactions in accordance with examples of the present disclosure. In some examples, the node-link interaction diagram 400 may correspond to a graph database or other relational database that is used to maintain known interactions between objects 112 and/or health conditions. The node-link interaction diagram 400 and/or the data forming the node-link interaction diagram 400 may be stored in the interaction information 132 of the memory 128, the health information memory 144, and/or the health information 236 location of the memory 208. Although shown in a node-link format, the data may be stored in any format that is capable of maintaining relationships between interactions between health conditions and/or objects 112. These relationships and links may, together, correspond to an interaction warning that is associated with a combination of at least two of the objects 112 if, and/or when, used together.

The node-link interaction diagram 400 shows a number of objects 112 that have been organized by medications 404A-404H, health conditions 408A-408C, vitamins 412, and foods 416A-416C. More specifically, the node-link interaction diagram 400 comprises drug nodes 404A-404H, health condition nodes 408A-408C, a vitamin node 412, and food nodes 416A-416C. Each of the nodes 404A-416C are connected to at least one other node 404A-416C via a link (shown as lines with double arrows). In some examples, the links may define a type of interaction between the various nodes 404A-416C. For instance, a dashed line may indicate a minor interaction between connected nodes 404A-416C, a thin solid line may indicate a moderate interaction between connected nodes 404A-416C, and a heavy solid line may indicate a severe interaction between connected nodes 404A-416C. Minor interactions may have the potential to cause a side effect according to a first predetermined percentage, moderate interactions may have the potential to cause a side effect according to a second predetermined percentage that is higher than the first predetermined percentage, and severe interactions may have the potential to cause a side effect according to a third predetermined percentage that is higher than the first and second predetermined percentages. The predetermined percentages may correlate, proportionately, to the risks associated with each interaction.

As illustrated in FIG. 4, the first set of clustered drug nodes 404A-404C includes a first drug node 404A (e.g., aspirin), a second drug node 404B (e.g., naproxen), and a third drug node 404C (ibuprofen). This first set of clustered drug nodes 404A-404C may be broadly classified as non-steroidal anti-inflammatory drugs (NSAIDs), and may be grouped in the first drug cluster 420. One or more other nodes 404D-416C may interact with a specific node 404A-404C in the first drug cluster 420 or with all of the nodes 404A-404C in first drug cluster 420. By way of example, a severe interaction may exist for a user 102 having the health condition asthma, identified as third health condition node 408C, with all NSAIDs, and is identified as such via a thick solid line between the third health condition node 408C and the first drug cluster 420. Similarly, the NSAIDs in the first drug cluster 420 may have a severe interaction known for user's who have GI toxicity, identified by the second health condition node 408B. In contrast, first food node 416A (e.g., alcohol) may only have a minor interaction with one of the NSAIDs in the first drug cluster 420 (e.g., third drug node 404C, or ibuprofen).

Outside of the first drug cluster 420, the vitamin node 412 (e.g., vitamin E) is shown to have a severe interaction with the first health condition node 408A (e.g., hepatobiliary dysfunction) and a moderate interaction with the fourth drug node 404D (e.g., warfarin).

The second drug cluster 424 is shown to include fifth drug node 404E (e.g., simvastatin) and sixth drug node 404F (atorvastatin). This second set of clustered drug nodes 404E-404F may be broadly classified as statins, and may be grouped in the second drug cluster 424. In some cases, two drugs may interact with one another in the form of redundant treatments. This type of interaction may result in doubledosing and such an interaction may be indicated by the link connecting fifth drug node 404E to sixth drug node 404F.

The third drug cluster 428 is shown as including seventh drug node 404G (e.g., cetirizine) and eighth drug node 404H (e.g., fexofenadine). This third set of clustered drug nodes 404G-404H may be broadly classified as antihistamines, and may be grouped together in third drug cluster 428.

Some of the nodes 404A-416C, or clusters 420-428, may have more than one connection to other nodes 404A-416C and/or clusters 420-428. For instance, minor interactions are shown to exist between first food node 416A (e.g., alcohol) and third drug node 404C (e.g., ibuprofen) and second drug cluster 424. Stated another way, a minor drug interaction may exist between alcohol and ibuprofen as well as between alcohol and statins. In presenting an interaction warning, the user 102 may be provided with information about the type of interaction, a severity of the interaction, and information about the health condition, medication, food, and/or vitamin associated with the interaction.

A severe interaction is shown to exist between the second food node 416B (e.g., grapefruit) and second drug cluster 424 (e.g., statins), while only a minor interaction is shown to exist between the second food node 416B and eighth drug node 404H. In determining that an interaction warning is associated between the health condition, medication, food, and/or vitamin, the interaction checking instructions 140, 244 may retrieve information from the node-link interaction diagram 400. The information may be used to identify the type, severity, and names of the objects 112 and/or health conditions associated with the interaction. In FIG. 4, a severe interaction is associated with grapefruit, or grapefruit juice, and statin drugs. However, a minor interaction is shown to exist between third food node 416C (e.g., orange) and eighth drug node 404H (e.g., fexofenadine). While only a limited number of interaction relationships are shown in the node-link interaction diagram 400 of FIG. 4, the node-link interaction diagram 400 may include any number of interaction relationships and the node-link interaction diagram 400 may be updated, modified, or maintained as more or fewer interactions are discovered. Examples of various presentations of interaction warnings are described in conjunction with FIGS. 5A-5H.

FIGS. 5A-5H show representative images of a device viewing area 504 of a mobile device 108 viewing an environment 114 in accordance with examples of the present disclosure. The device viewing area 504 may correspond to at least one display device 210 of the health interaction checking system 100. In another example, where the mobile device 108 is configured as a head-mounted device 108A, the device viewing area 504 may correspond to clear lens of an AR headset. In this latter example, the augmented reality combined presentation may comprise real images of the environment 114 seen through the lens and additional information (e.g., warnings, icons, text, etc.) is projected directly onto the retina of the user 102. In each example, the mobile device 108 may include an edge 508, or perimeter border, that separates the device viewing area 504 from the real viewing area 512. The real viewing area 512 may correspond to an unimpeded area between the user 102 and the objects 112 in the environment 114. The mobile device 108 is capable of providing the augmented reality combined presentations described in conjunction with FIGS. 5A-5H, whether in AR, MR, or VR.

For the sake of clarity in description, FIGS. 5A-5H will be described in conjunction with a mobile device 108 having a display screen 252 (e.g., of a display device 210) and where the device viewing area 504 includes images of the environment 114 and the certain objects 112 that are rendered to the display screen 252. However, in examples where the mobile device 108 is configured to include a projector 224 (e.g., that projects light and information onto the retina of a user 102), the device viewing area 504 may correspond to a clear or translucent lens (e.g., allowing the real, non-generated, images of the environment 114 and objects 112 to pass therethrough, etc.) and the icons 528-540, 552, 558A-558C, lines 544, and windows 548, 554, 556, 566 may be generated digital visual elements that are projected onto the retina of the user 102 by the projector 224 in specific areas of the device viewing area 504.

Figure 5A:
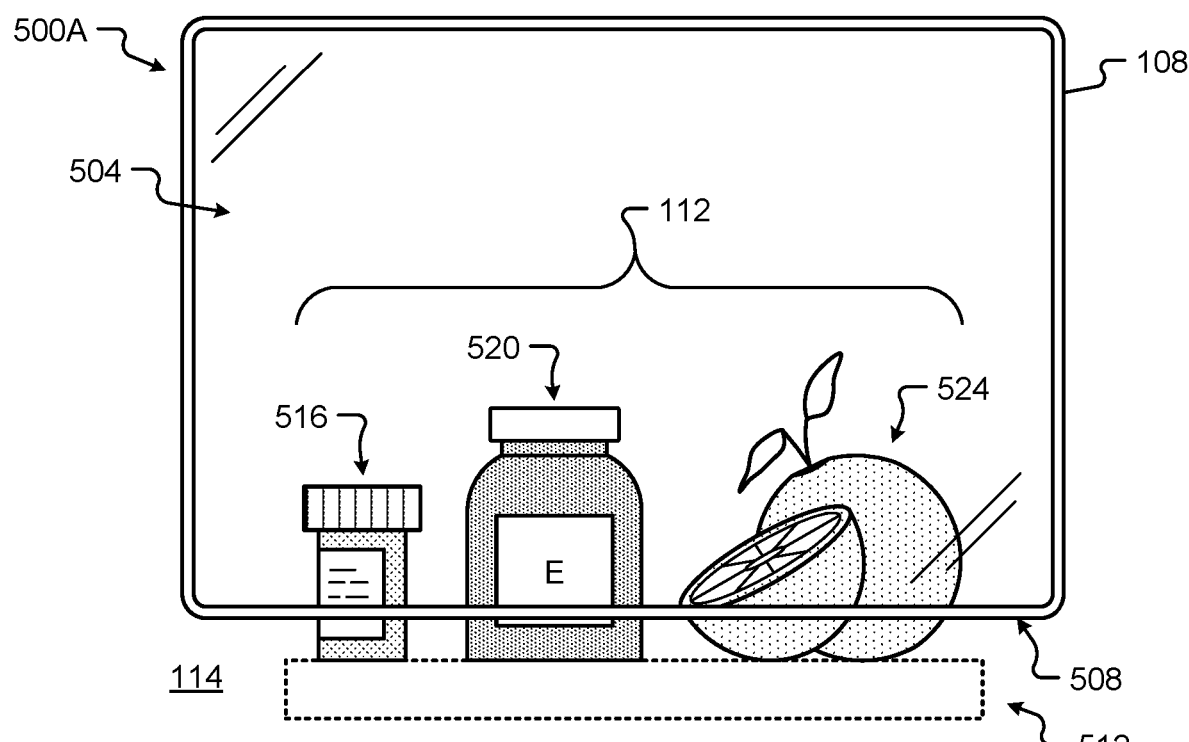
FIG. 5A is a representative image of a viewing area of a mobile device in a first presentation viewing an environment in accordance with examples of the present disclosure.

FIG. 5A is a representative image of a device viewing area 504 of a mobile device 108 in a first presentation 500A viewing an environment 114 in accordance with examples of the present disclosure. In FIG. 5A, the objects 112 are shown in the device viewing area 504 of the mobile device 108 to include a medication container 516, a vitamin container 520, and a food 524. In some examples, as the camera 228 of the mobile device 108 records images of the environment 114, the mobile device 108 may render these real-time images to the display screen 252 of the display device 210, which is visible in the device viewing area 504. The medication container 516 may correspond to a typical prescription bottle or container. Similarly, the vitamin container 520 may correspond to a package or bottle with identification markings (e.g., listing the ingredients, contents, brand names, etc.) associated with the vitamin, or vitamins, contained therein. The food 524 may be visible on a menu, on an outside of a package, removed from a package or cover, before cooking, after cooking, and/or combinations thereof. As shown in FIGS. 5A-5E, the food 524 is represented as a whole grapefruit and a cut portion of a grapefruit. However, the examples described herein are not limited to food 524 in the form of fruit, or fruit juices, and any food, beverage, or meal may be identified based on images collected by the mobile device 108 (e.g., the cameras 228 of the mobile device 108). In some examples, FIG. 5A may correspond to a view, observed at the mobile device 108, of the objects 112 in the environment 114 prior to the objects 112 being identified.

Figure 5B:
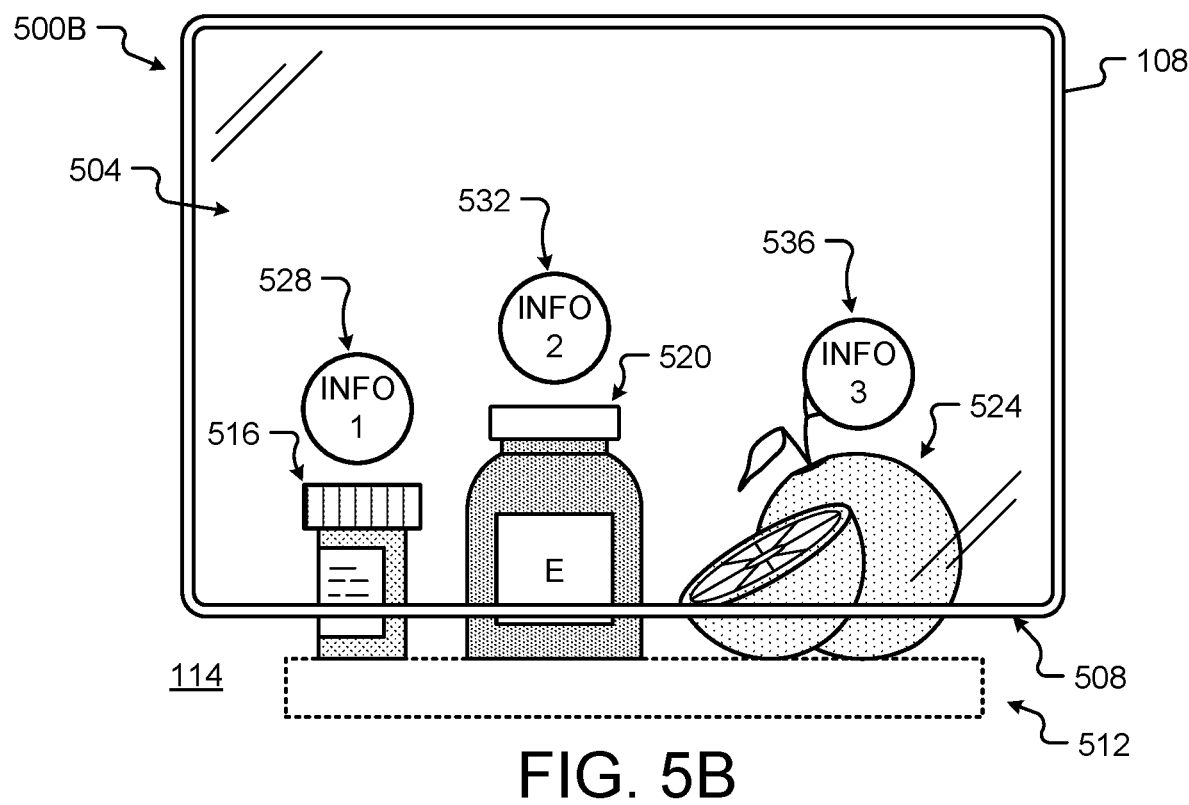
FIG. 5B is a representative image of a viewing area of a mobile device in a second presentation viewing an environment with digitally overlaid information in accordance with examples of the present disclosure.

FIG. 5B is a representative image of the device viewing area 504 of the mobile device 108 in a second presentation 500B viewing an environment 114 with digitally overlaid information 528, 532, 536 shown in an augmented presentation. Specifically, the first information display icon 528 is shown rendered to a portion of the device viewing area 504 adjacent the medication container 516, the second information display icon 532 is shown rendered to a portion of the device viewing area 504 adjacent the vitamin container 520, and the third information display icon 536 is shown rendered to a portion of the device viewing area 504 adjacent the food 524. As the user 102 moves the mobile device 108 relative to the objects 112, and the position of the objects 112 in the device viewing area 504 change, the information display icons 528-536 may move independently, or together, to remain adjacent a respective object 516-524. When a specific object 516-524 is no longer visible in the device viewing area 504, the respective information display icon 528-536 may no longer be rendered in the device viewing area 504. The information display icons 528-536 may provide information about the corresponding adjacent object 516-524. For instance, the first information display icon 528 may provide information about the medication container 516, the second information display icon 532 may provide information about the vitamin container 520, and the third information display icon 536 may provide information about the food 524. The information provided may correspond to an icon indicating that a respective object 516-524 has been successfully scanned and/or identified (e.g., a checkmark, a color, an emoji, a character or character string, a word, a phrase, etc., and/or combinations thereof) a text-based pop-up including details of the identified respective object 516-524 (e.g., a name, brand name, generic name, etc., and/or combinations thereof), a historical informational message about the identified respective object 516-524 (e.g., "this object was previously scanned," "this object is in your medicine cabinet," "this is a new object," etc.), and/or the like. This information may be retrieved (e.g., by the mobile device 108) from the health information memory 144, the user information 232, the health information 236, and/or the health information data structure 300.

Figure 5C:
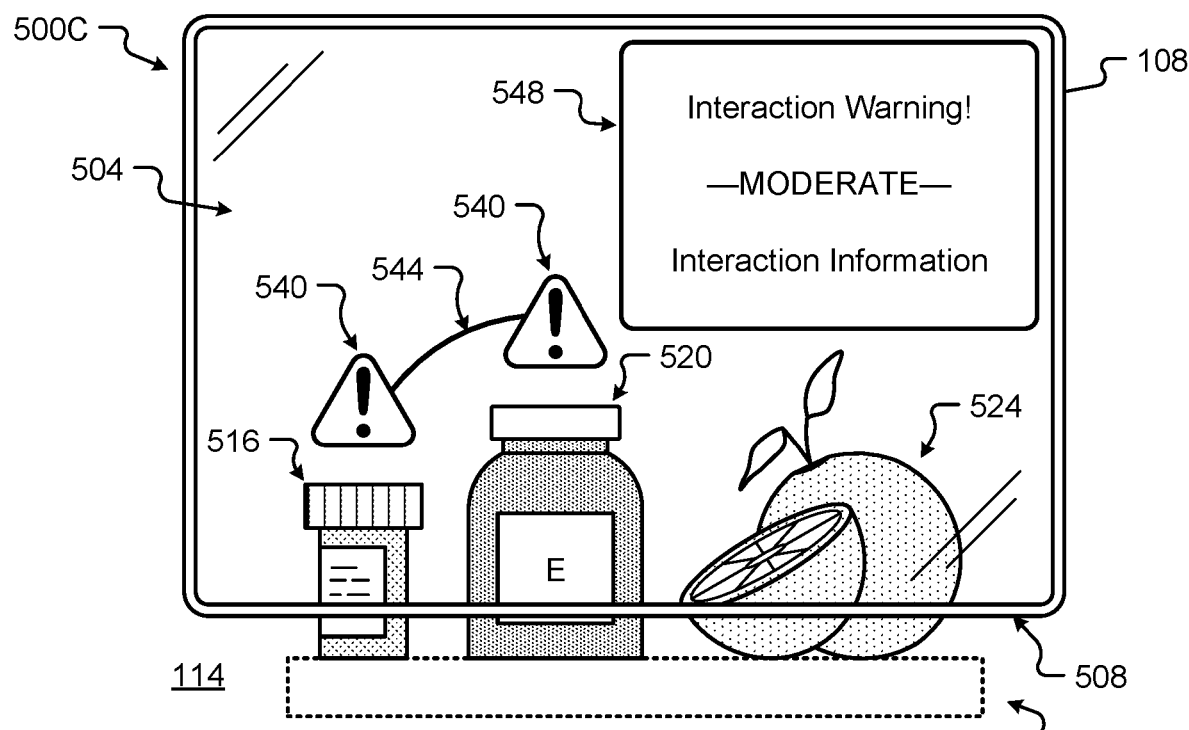
FIG. 5C is a representative image of a viewing area of a mobile device in a third presentation viewing an environment with digitally overlaid information including a first type of interaction warning in accordance with examples of the present disclosure.

FIG. 5C is a representative image of a device viewing area 504 of a mobile device 108 in a third presentation 500C viewing an environment 114 with digitally overlaid information including a first type of interaction warning in accordance with examples of the present disclosure. In FIG. 5C, the mobile device 108 has determined that a moderate interaction and an interaction warning is associated with a combination of the medication (in the medication container 516) and the vitamin (in the vitamin container 520) in the environment 114. For the sake of example, this moderate interaction may correspond to the interaction between warfarin and vitamin E illustrated as the fourth drug node 404D and the vitamin node 412, respectively, which are linked together in the node-link interaction diagram 400 of FIG. 4. In response to this determination, the display device 210 may render one or more informational images 540-548 in the device viewing area 504. For example, a general interaction warning icon 540 (e.g., shown in the form of an exclamation point in a triangular shape) may be rendered adjacent the respective objects 516, 520 having the interaction warning and a interaction warning window 548 is rendered to a portion of the device viewing area 504 in view of the user 102. The general interaction warning icons 540 may be joined together with an icon link line 544. As the mobile device 108 is moved relative to the objects 112 in the environment 114, and the position of the objects 112 in the device viewing area 504 change, the general interaction warning icons 540 may move independently, or together, to remain adjacent their respective objects 516, 520. Additionally or alternatively, the icon link line 544 may expand, or move, remaining linked to the general interaction warning icons 540 as the mobile device 108 is moved or the objects 516, 520 in the environment 114 are moved. The interaction warning window 548 may be configured as a pop-up window, or toast, including details about the interaction warning. These details may include an alert or health hazard warning (e.g., "Interaction Warning!"), indicating a severity of the health hazard (e.g., as "minor," "moderate," and/or "severe," etc.) that is associated with the determined interaction warning, and other information including potential risks, drugs involved in the interaction, side effects associated with the interaction, other related interactions, and/or the like. The interaction warning window 548, and any other window 554, 556, 566 or icon 528-540, 552, 558A-558C, etc., may be color-coded to visually indicate a level of severity for the interaction warning (e.g., minor severity being colored with a "yellow" fill or highlight, moderate severity being colored with an "orange" fill or highlight, and severe, or deadly, severity being colored with a "red" fill or highlight).

Figure 5D:
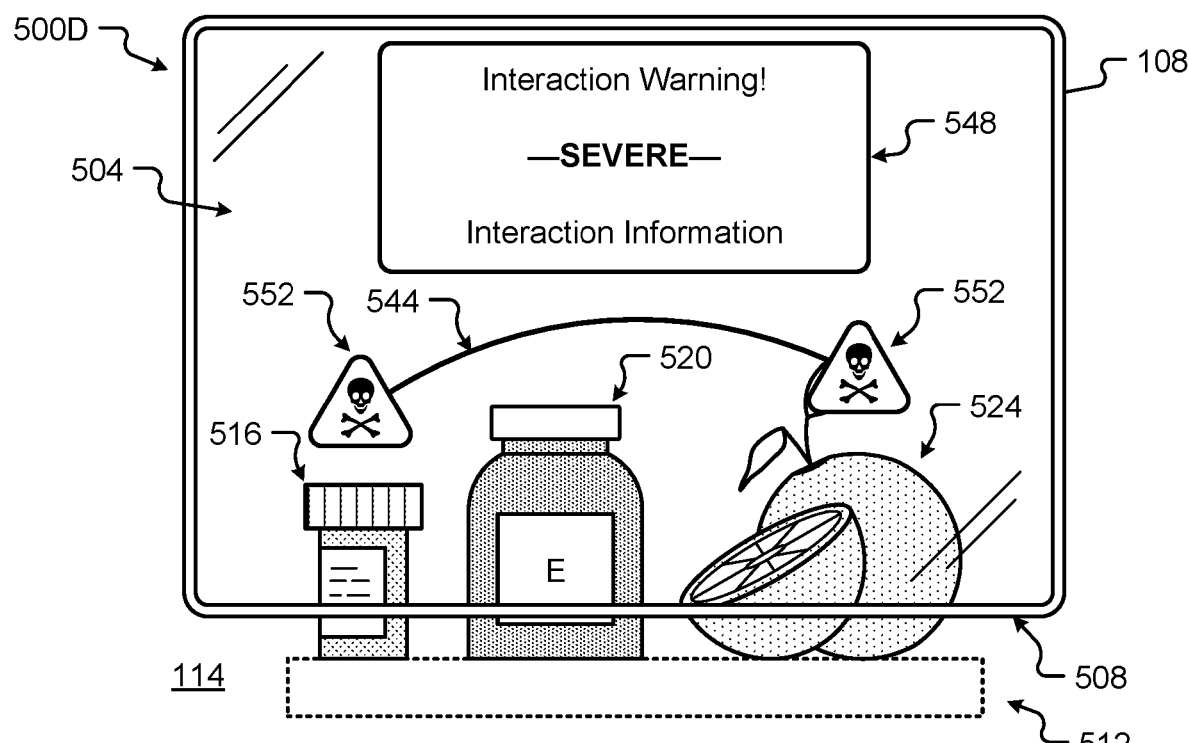
FIG. 5D is a representative image of a viewing area of a mobile device in a fourth presentation viewing an environment with digitally overlaid information including a second type of interaction warning in accordance with examples of the present disclosure.

FIG. 5D is a representative image of a device viewing area 504 of a mobile device 108 in a fourth presentation 500D viewing an environment 114 with digitally overlaid information including a second type of interaction warning in accordance with examples of the present disclosure. In FIG. 5D, the mobile device 108 has determined that a severe interaction and an associated interaction warning is associated with a combination of the medication (in the medication container 516) and the food 524 (e.g., grapefruit) in the environment 114. For instance, this severe interaction may correspond to the interaction between the statins and the grapefruit (e.g., grapefruit juice, etc.) illustrated as the second drug cluster 424 and the second food node 416B, respectively, and which are linked together in the node-link interaction diagram 400 of FIG. 4. In response to this determination, the display device 210 may render one or more informational images 548, 552 in the device viewing area 504. As shown in FIG. 5D, a severe interaction warning icon 552 (e.g., shown in the form of skull and crossbones symbol in a triangular shape) may be rendered adjacent the respective objects 516, 524 having the severe interaction warning and an interaction warning window 548 is rendered to a portion of the device viewing area 504 in view of the user 102. In some examples, the symbol in the icons 540, 552 may match a type of side effect for the interaction. For instance, where the side effect is toxicity, the symbol may be illustrated as a "radioactive" symbol, where the health risk is death, the symbol may be the "skull and crossbones," etc. In any event, the severe interaction warning icons 552 may be joined together with an icon link line 544. As the mobile device 108 is moved relative to the objects 112 in the environment 114, and the position of the objects 112 in the device viewing area 504 change, the severe interaction warning icons 552 may move independently, or together, to remain adjacent their respective objects 516, 524. The icon link line 544 may expand, or move, remaining linked to the severe interaction warning icons 552 as the mobile device 108 is moved or the objects 516, 524 in the environment 114 are moved. Similar to the interaction warning window 548 described above, the details may indicate the severity of the health hazard associated with the interaction. In this case, the severity level of the interaction warning is "severe." Other information in the interaction warning window 548 may include potential risks, names of the foods, drugs, and/or vitamins involved in the interaction, side effects associated with the interaction, other related interactions, etc.

Figure 5E:
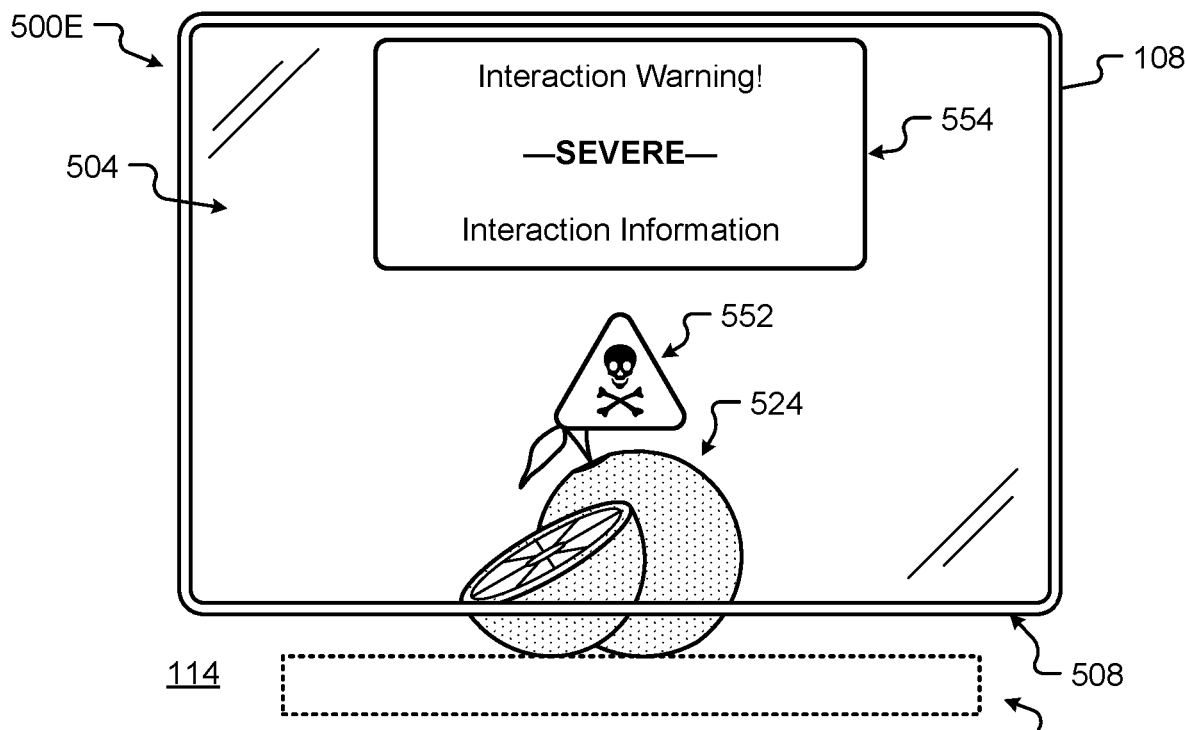
FIG. 5E is a representative image of a viewing area of a mobile device in a fifth presentation viewing an environment with digitally overlaid information including a determined interaction warning in accordance with examples of the present disclosure.

FIG. 5E is a representative image of a device viewing area 504 of a mobile device 108 in a fifth presentation 500E viewing an environment 14 with digitally overlaid information including a determined interaction warning in accordance with examples of the present disclosure. In some examples, the mobile device 108 may determine an interaction for an object 112 based on historical data (e.g., previously scanned objects 112), user information, health information 340 (e.g., preexisting conditions, treatments, etc.), and/or other information retrieved from the health information memory 144, user information 232, health information 236, and/or health information memory 144. As shown in FIG. 5E, only a food 524 is shown in the device viewing area 504 of the mobile device 108. However, since the mobile device 108 and/or the health and interaction server 116 are each capable of maintaining, independently or together, information regarding previously identified objects (e.g., in the identified objects field 312 of the health information data structure 300) and health information 340 of the user 102 (e.g., stored in the health information data structure 300, etc.), the mobile device 108 and/or the health and interaction server 116 (e.g., via the interaction checking instructions 140, 244, etc.) can access this data and determine whether an interaction exists between a combination of any object 112 detected in the device viewing area 504 and the data. In FIG. 5E, the food 524 is shown as a grapefruit and a severe interaction warning icon 552 is rendered adjacent the food 524. In addition a determined interaction warning window 554 is rendered to a portion of the device viewing area 504 in view of the user 102. In one example, the determined interaction warning window 554 may be presented after the food 524 is visible in the device viewing area 504. Once the food 524 is identified, the interaction checking instructions 144, 244, when executed by the processor 124, 204 may determine that the user 102 has been prescribed a statin drug (e.g., by automatically retrieving data stored in the medications field 324 of the health information data structure 300) and then determining an interaction warning is associated with a combination of the statin and the food 524 if, or when, used together. Similar determinations may be made for medications and vitamins based on health information 340 of the user 102.

Figure 5F:
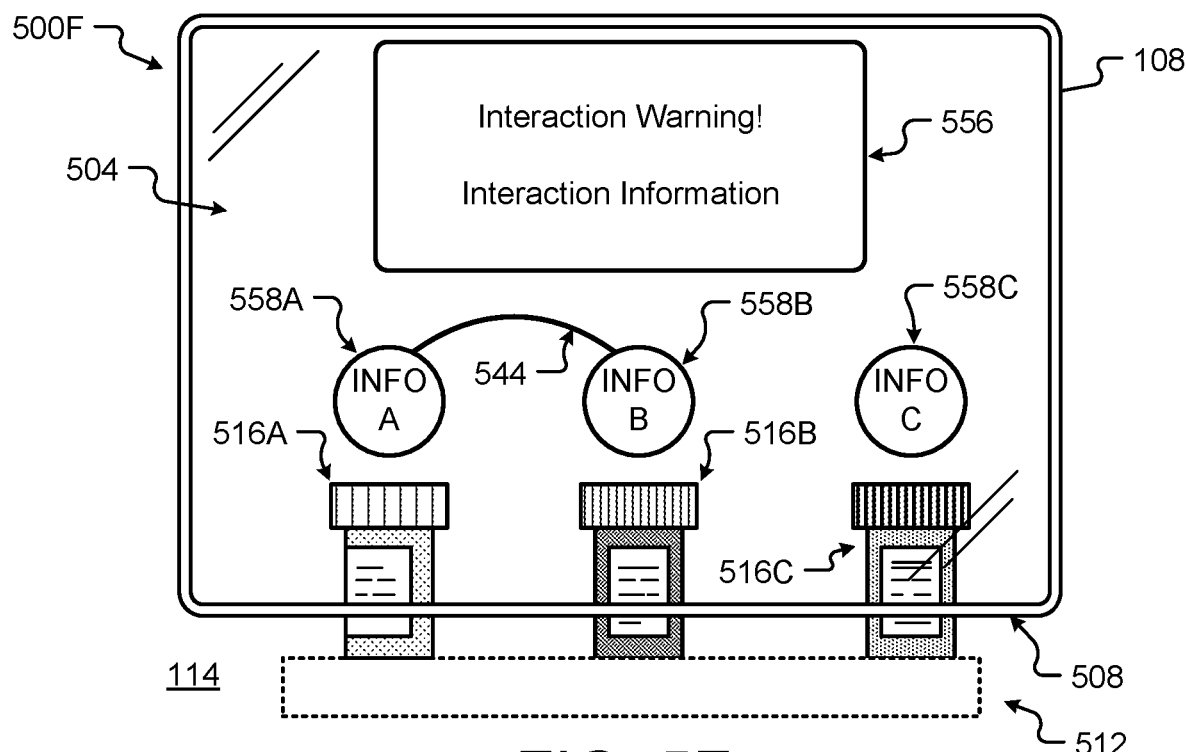
FIG. 5F is a representative image of a viewing area of a mobile device in a sixth presentation viewing an environment with digitally overlaid information including a comparative interaction warning in accordance with examples of the present disclosure.

FIG. 5F is a representative image of a device viewing area 504 of a mobile device 108 in a sixth presentation 500F viewing an environment 114 with digitally overlaid information including a comparative interaction warning in accordance with examples of the present disclosure. In some examples, the interaction checking instructions 140, 244, when executed by the respective processor 124, 204, may determine interactions and interaction warnings between medications, foods, and/or vitamins (e.g., objects 112) without accessing health information 340 of a user 102. Stated another way, the methods described herein may operate in an unauthenticated, or guest, state where interactions between objects 112 identified are determined without requiring inclusion of health information 340 retrieved from a user account. In FIG. 5F, medication containers 516A-516C are shown in the device viewing area 504 of the mobile device 108. In response to identifying each of the medication containers 516A-516C, the interaction checking instructions 140, 244, when executed by a respective processor 124, 204, may determine that an interaction warning exists between two, or more, of the medications in the medication containers 516A-516C. The details of the interaction warning may be provided in the comparative interaction warning window 556, which is similar to the interaction warning window 548, etc. As illustrated in FIG. 5F, a first object information display icon 558A is rendered in the device viewing area 504 adjacent the first medication container 516A and a second object information display icon 558B is rendered in the device viewing area 504 adjacent the second medication container 516B. The icon link line 544 spanning between the first object information display icon 558A and the second object information display icon 558B may serve to indicate that the interaction warning is associated with a combination of the medication in the first medication container 516A and the medication in the second medication container 516B. A third object information display icon 558C may be rendered adjacent the third medication container 516C. The object information display icons 558A-558C may provide information that is similar, if not identical, to the information described in conjunction with any of the information display icons 528-536, interaction warning icons 540, 552 described above and in conjunction with FIGS. 5B-5E.

Figure 5G:
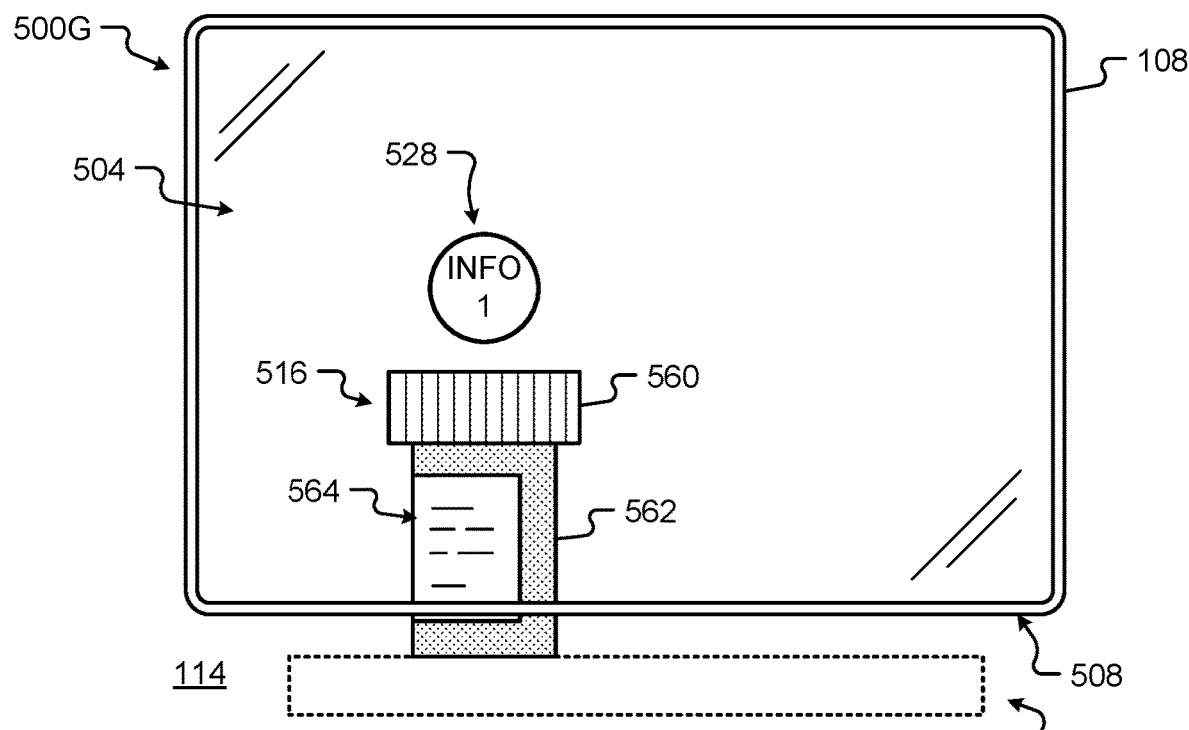
FIG. 5G is a representative image of a viewing area of a mobile device in a seventh presentation viewing an environment with digitally overlaid information highlighting information about an object in accordance with examples of the present disclosure.
Figure 5H:
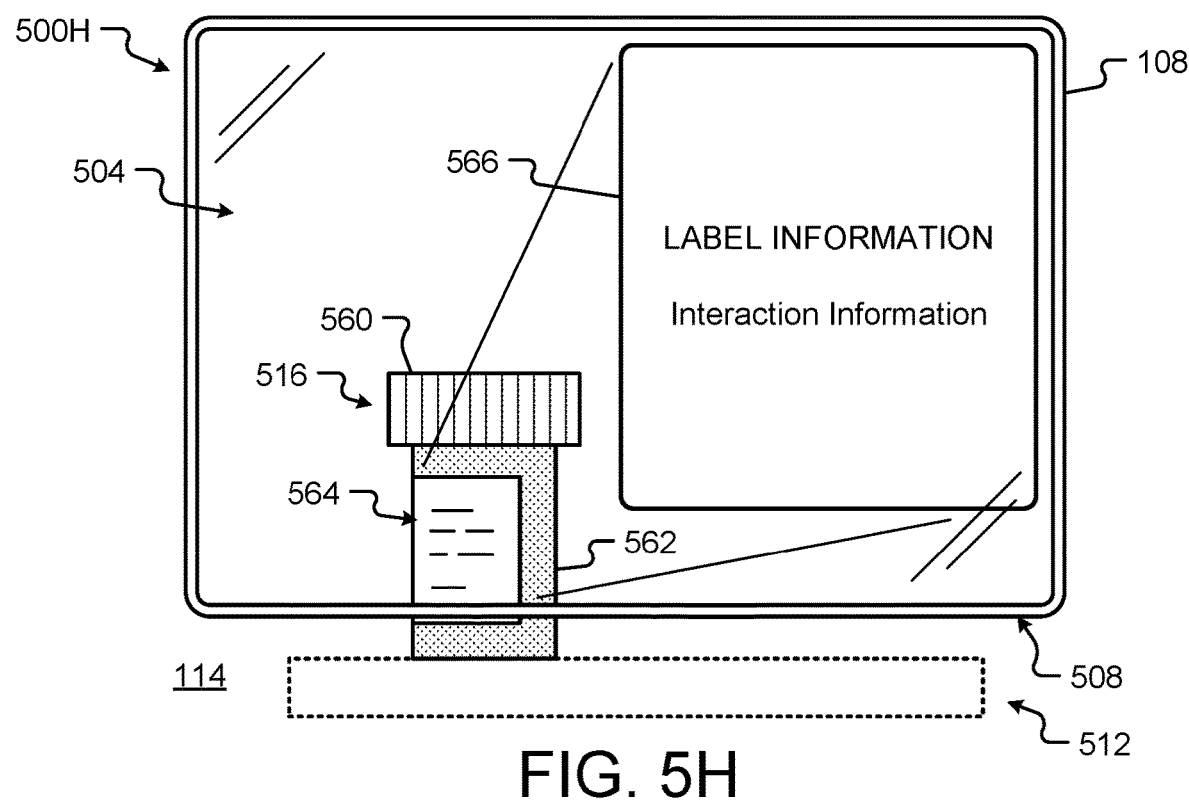
FIG. 5H is a representative image of a viewing area of a mobile device in an eighth presentation viewing an environment with digitally overlaid information adjusting a presentation of information about an object in accordance with examples of the present disclosure.

FIGS. 5G-5H show representative images of a device viewing area 504 including a medication container 516. The medication container 516 may include a cap 560, a body 562, and a label 564. The body 562 may include a cavity, or chamber, that receives and holds a medication (e.g., powder, pill, tablet, liquid, etc.). As shown in the seventh presentation 500G of FIG. 5G, a first information display icon 528 is rendered adjacent the medication container 516. In some examples, this first information display icon 528 may indicate that the medication container 516 has been successfully identified. In some examples, the interaction checking instructions 140, 244, when executed by a respective processor 124, 204, may determine, based on health information 340 retrieved about the user 102, that the user 102 has a vision impairment or disability. This information may be stored, for example, in the preexisting condition field 328 of the health information data structure 300. Next, and as shown in the eighth presentation 500H of FIG. 5H, the interaction checking instructions 140, 244, when executed by a respective processor 124, 204, may adjust a contrast, a color, and a size of the information presented based on the vision disability. For instance, the adjusted information presentation window 566 may be rendered to the device viewing area 504 of the mobile device 108 providing an enhanced viewing area for the label 564 and/or the medication container 516. In some examples, the adjusted information presentation window 566 may increase a legibility of the label 564 for the user 102. In one example, the adjusted information presentation window 566 may include additional information not found on the label 564 (e.g., such as information stored in the interaction information 132, etc.) and provide further detail about the medication in the medication container 516. Similar informational presentations may be provided for foods and vitamins scanned by the camera 228 of the mobile device 108.

Figure 6:
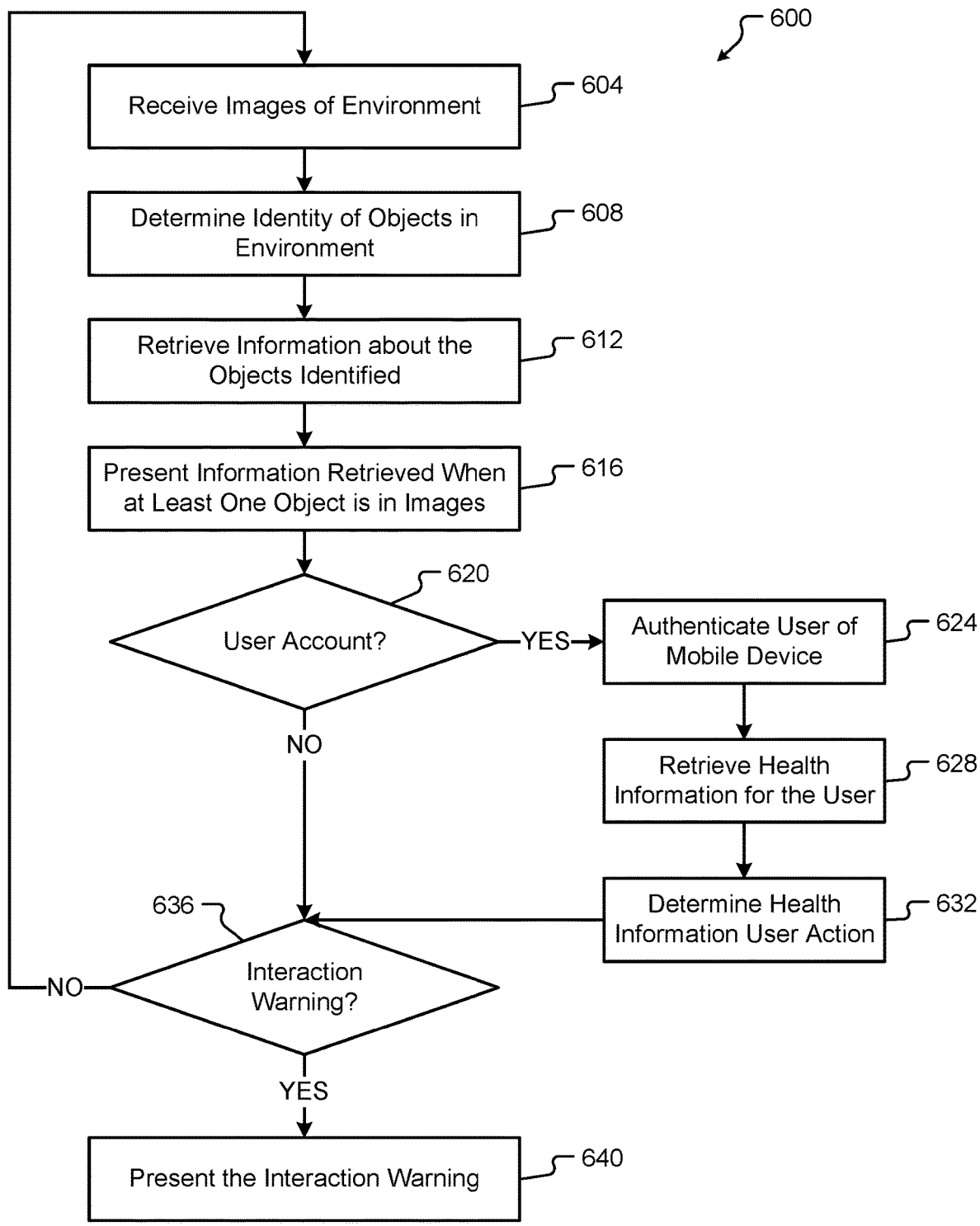
FIG. 6 is a flow diagram of a method for checking for health interactions and presenting information to a user in accordance with examples of the present disclosure.

FIG. 6 is a flow diagram of a method 600 for checking for health interactions and presenting information to a user 102 in accordance with examples of the present disclosure. One or more of the methods 600, 632 described herein may be run as a set of instructions on the mobile device 108, the health and interaction server 116, and/or some other device or server of the health interaction checking system 100. In some examples, the set of instructions may be part of an application installed on one or more mobile devices 108 and/or health and interaction server 116 that manages the behavior and/or operation of mobile devices 108 in the health interaction checking system 100.

The method 600 begins by receiving images of an environment 114 (step 604). As provided above, the images of the environment 114 may include one or more objects 112. In some examples, step 604 may include receiving digital images of one or more objects 112 from at least one camera 228 of a mobile device 108. Based on the digital images received, the method 600 may continue by determining an identity of the one or more objects 112 in the environment 114 (step 608). The identity of the objects 112 may be determined by shape recognition, image recognition, text recognition, artificial intelligence for image classification and object recognition, and/or combinations thereof. In some examples, this determination may include comparing information in the digital images received with other known images, image portions, and/or trained templates. The identification may be determined according to a percentage level of confidence. In some examples, these percentages of confidence may be presented to the user 102 (e.g., via the display device 210 and/or the projector 224) allowing the user 102 to accept the identification as positive or indicate that the identification appears incorrect.

Upon determining the identity of one or more objects 112 from the digital images, the method 600 may proceed by retrieving information about the one or more objects 112 identified (step 612). The information may include, but are in no way limited to, a name, known risks or side effects, prescription information, interaction information, and/or any other information described herein for the one or more objects 112. This information may be presented when at least one object 112 of the one or more objects 112 is visible in the digital images (step 616). Said another way, when at least one object 112 of the objects 112 is detected (e.g., within the detection range 110 of the camera 228 of the mobile device 108) the display device 210 may render the information about the at least one object 112 in the device viewing area 504. In some examples, the information may be rendered adjacent the at least one object 112 in the device viewing area 504. In this manner, the information is presented dimensionally close to indicate that the information is associated with a particular object 112 in the device viewing area 504, especially when multiple objects 112 (e.g., having multiple information presentations) are in the device viewing area 504.

Next, the method 600 may continue by determining whether the user 102 of the mobile device 108 is registered with a user account, such as user health or medical account (step 620). In one example, this determination may include referring to a registration status field 308 of a health information data structure 300 associated with the user 102. The health information data structure 300 may be stored in the memory 128 of the health and interaction server 116, in the health information memory 144, and/or in the memory 208 of the mobile device 108. The registration status field 308 may indicate a registration status (e.g., registered, unregistered, etc.) for one or more user accounts associated with the user 102. If the user 102 is not registered with a user account, the method 600 may proceed to step 636 to determine whether the information retrieved in step 612 includes an interaction warning.

In the event that the user is determined to be registered with a user account in step 620, the method may proceed to authenticate the user 102 of the mobile device 108 (step 624). The authentication may comprise using authentication credentials and/or identification information for the user 102 to access a secure data storage memory location. The authentication credentials may be stored as authorization information 136 in the memory 128 of the health and interaction server 116 and/or as user information 232 in the memory 208 of the mobile device 108. In one example, the user 102 may provide the authentication credentials from the mobile device 108 to the health and interaction server 116. At the health and interaction server 116, the authentication credentials may be verified (e.g., when the authentication credentials match, etc.) allowing access to health information 340 for the user 102 (e.g., stored in the health information memory 144, etc.).

Once authenticated, the method 600 may continue by retrieving (e.g., from a user account database such as the health information memory 144, etc.) heath information 340 associated with the user 102 (step 628). As provided above, the health information 340 may include at least one medical treatment, prescribed medication, preexisting condition, and/or state of health associated with the user 102. In some examples, the method 600 may determine an action, behavior, or presentation for the mobile device 108 that is based on the health information 340 retrieved for the user 102 (step 632). Step 632 is described in conjunction with FIG. 7.

At step 636, the method 600 determines whether an interaction warning is associated with a combination of the at least two objects 112 used together and/or between at least one object 112 and the health information 340 for a user 102. In some examples, the method 600 may refer to the node-link interaction diagram 400 to determine, based on at least one of the information retrieved (e.g., in step 612) and/or the health information 340 retrieved, whether an interaction warning exists between any two nodes 404A-428 that apply to the at least two objects 112 used together and/or between the at least one object 112 and the health information 340 for the user 102. If no interaction warning exists, the method 600 may end or return to step 604. However, when an interaction warning exists, the method 600 may proceed by presenting the interaction warning (step 640). The interaction warning may be presented in any manner described herein and especially as illustrated in conjunction with FIGS. 5B-5H.

Figure 7:
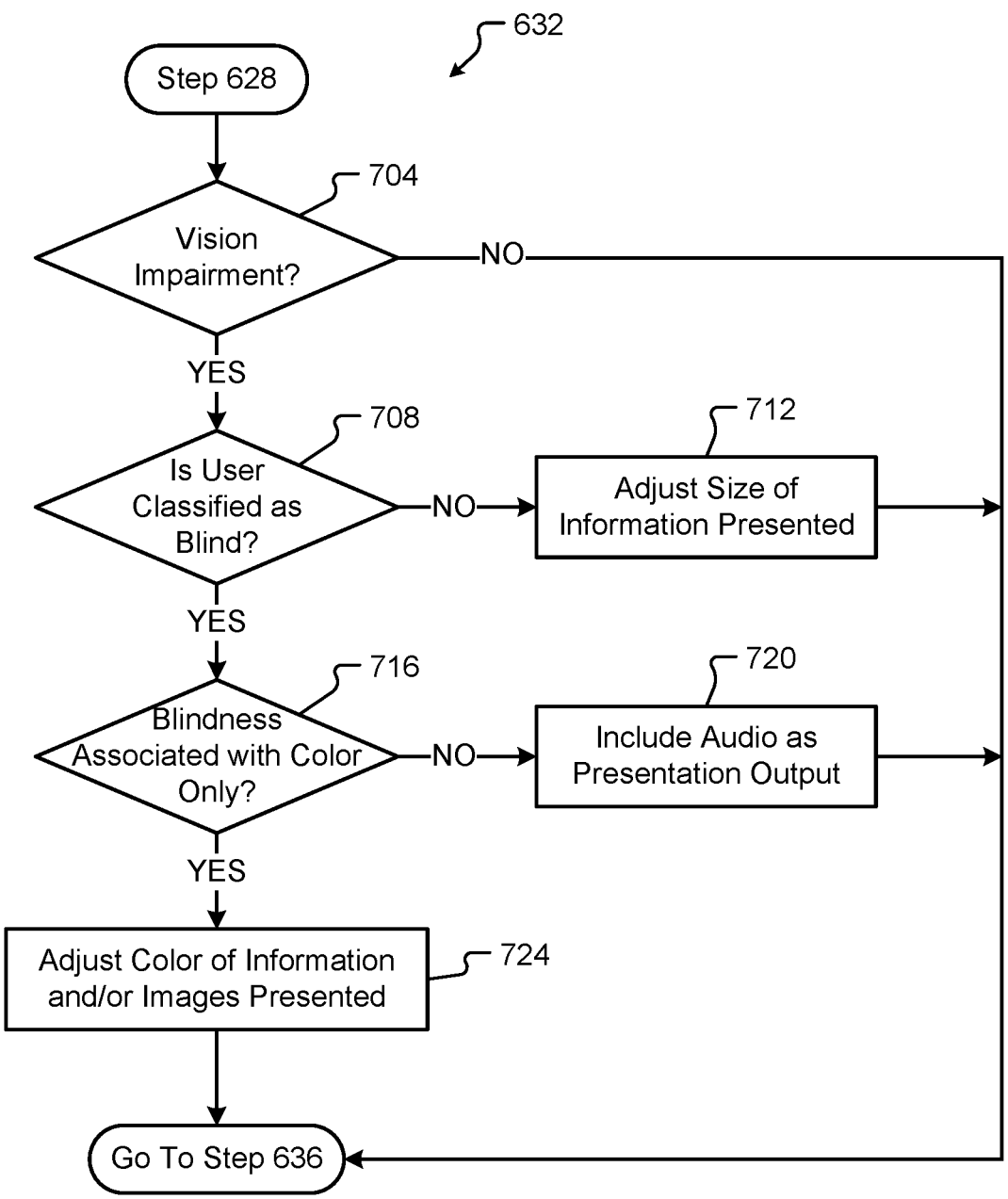
FIG. 7 is a flow diagram of a method for adjusting an output to a user based on health information retrieved for the user in accordance with examples of the present disclosure.

FIG. 7 is a flow diagram of a method 632 for adjusting an output to a user 102 based on health information 340 retrieved for the user 102 in accordance with examples of the present disclosure. The method 632 begins by determining whether the user 102 has a vision impairment, or disability (step 704). The vision impairment may be stored as information in the preexisting condition field 328 and/or the state of health field 332 of the health information data structure 300. If there is no recorded vision impairment for the user 102 in the health information 340, the method 632 may proceed to step 636 of the method 600 described in conjunction with FIG. 6.

In the event that the user 102 is determined to have a vision impairment, the method 632 may continue by determining a type of impairment an action for the mobile device 108. For instance, the method 632 may determine whether the user 102 is classified as blind (e.g., having a visual acuity worse than 20/400, or 20/200 for legally blind, etc.) in step 708, if not the method 632 may proceed to step 712 and adjust a size of the information presented by the mobile device 108. This adjustment may correspond to the adjustment of information found on a medication container 516 label 564, as described in conjunction with FIGS. 5G-5H. In some examples, this adjustment may be made for users 102 having an astigmatism, nearsightedness, farsightedness, cataracts, or other non-blindness related visual acuity challenges. The method 632 may proceed to step 716 when the user 102 is classified as blind in step 708. In step 716, the method 632 may determine whether the blindness of the user 102 is associated with color only. Stated another way, the user 102 may have perfect visual acuity (e.g., 20/20) but may be unable to differentiate between two or more colors (e.g., red and green, blue and yellow, yellow and red, blue and green, purple and red, etc.). This impairment may be referred to herein as color-blindness and information regarding the type of color-blindness may be stored in the preexisting condition field 328 of the health information data structure 300. If the user 102 is determined not to be color-blind, the method 632 may proceed to step 720 and include an audio output as part of the interaction warning presentation. The audio output may be presented to a user 102 via one or more speakers 220 of the mobile device 108. In the event that the user 102 is determined to be color blind, however, the method 632 may proceed to adjust the color, or contrast, of the information and/or images that form the presentation (step 724). The various adjustments described in conjunction with the method 632 may be combined in any manner possible, for example, when a user 102 is determined to have multiple vision impairments. Additionally or alternatively, the adjustments may be provided to a user 102 based on preferences set and/or stored as user information 232 in the memory 208 of the mobile device 108. Once the actions or presentation adjustments are determined, if any, the method 632 may continue by proceeding to proceed to step 636 of the method 600 described in conjunction with FIG. 6.

Any of the steps, functions, and operations discussed herein can be performed continuously and automatically.

While the flowcharts have been discussed and illustrated in relation to a particular sequence of events, it should be appreciated that changes, additions, and omissions to this sequence can occur without materially affecting the operation of the disclosed examples, configuration, and aspects.

The exemplary systems and methods of this disclosure have been described in relation to AR, MR, and/or VR presentations that are rendered and/or projected by display devices. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

A number of variations and modifications of the disclosure can be used. It would be possible to provide for some features of the disclosure without providing others.

References in the specification to "one example," "an example," "some examples," etc., indicate that the example described may include a particular feature, structure, or characteristic, but every example may not necessarily include the particular feature, structure, or characteristic. Moreover, such phrases are not necessarily referring to the same example. Further, when a particular feature, structure, or characteristic is described in conjunction with one example, it is submitted that the description of such feature, structure, or characteristic may apply to any other example unless so stated and/or except as will be readily apparent to one skilled in the art from the description. The present disclosure, in various examples, configurations, and aspects, includes components, methods, processes, systems and/or apparatus substantially as depicted and described herein, including various examples, subcombinations, and subsets thereof. Those of skill in the art will understand how to make and use the systems and methods disclosed herein after understanding the present disclosure. The present disclosure, in various examples, configurations, and aspects, includes providing devices and processes in the absence of items not depicted and/or described herein or in various examples, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more examples, configurations, or aspects for the purpose of streamlining the disclosure. The features of the examples, configurations, or aspects of the disclosure may be combined in alternate examples, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed example, configuration, or aspect. Thus, the following claims are hereby incorporated into this Detailed Description, with each claim standing on its own as a separate preferred example of the disclosure.

Moreover, though the description of the disclosure has included description of one or more examples, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative examples, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

It is to be appreciated that any feature described herein can be claimed in combination with any other feature(s) as described herein, regardless of whether the features come from the same described example.

As used herein, the singular forms "a," "an," and "the" are intended to include the plural forms as well, unless the context clearly indicates otherwise. It will be further understood that the terms "include," "including," "includes," "comprise," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B, and C together. When each one of A, B, and C in the above expressions refers to an element, such as X, Y, and Z, or a class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The terms "determine," "calculate," "compute," and variations thereof, as used herein, are used interchangeably and include any type of methodology, process, mathematical operation, or technique.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and this disclosure.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

A number of implementations have been described. Nevertheless, it will be understood that additional modifications may be made without departing from the scope of the inventive concepts described herein, and, accordingly, other examples are within the scope of the following claims.

What is claimed is:

1. A mobile device, comprising: a camera;
   a display device;
   a processor coupled to the camera and the display device; and a memory coupled with and readable by the processor and storing therein instructions that, when executed by the processor, cause the processor to:
   receive, from the camera, images of an environment;
   determine, from the images of the environment received, an identity of at least two objects in the environment, wherein a first object of the at least two objects corresponds to at least one of a medication and a vitamin and a second object of the at least two objects corresponds to a food;
   retrieve, from a memory device based on the identity of the at least two objects in the environment, information about the at least two objects;
   determine, based on the information about the at least two objects, that an interaction warning is associated with a combination of the at least two objects used together;
   present, by the display device as the images of the environment are received and while the second object is present in the images of the environment, the interaction warning adjacent an image of the second object in the images of the environment; and
   present, by the display device as the images of the environment are received, a health hazard warning when both of the at least two objects appear in the images of the environment at a same time,
   wherein the health hazard warning comprises a graphical icon linking both of the at least two objects together.

2. The mobile device of claim 1, wherein the instructions further cause the processor to:
   present, by the display device as the images of the environment are received from the camera, the information about at least one object of the at least two objects when the at least one object appears in the images of the environment.

3. The mobile device of claim 2, wherein the mobile device comprises a head mounted display, and wherein presenting the information and the interaction warning comprises projecting light comprising the information and the interaction warning directly onto a retina of a user of the head mounted display.

4. The mobile device of claim 2, wherein the display device comprises a display screen, and wherein presenting the information and the interaction warning comprises rendering the images of the environment to the display screen as the images of the environment are received and rendering images of the information and the interaction warning in an augmented reality combined presentation.

5. The mobile device of claim 1, wherein the instructions further cause the processor to:
   authenticate a user of the mobile device; and
   retrieve, from a user account database in response to authenticating the user, heath-health information associated with the user, wherein the health information comprises at least one medical treatment, prescribed medication, preexisting condition, and state of health associated with the user.

6. The mobile device of claim 5, wherein the health information comprises a vision disability as the preexisting condition, and wherein presenting the information about each object when each object appears in the images of the environment further comprises at least one of adjusting a contrast, a color, and a size of the information presented based on the vision disability.

7. The mobile device of claim 5, wherein the instructions further cause the processor to:
   determine, based on the information about the at least two objects and the health information, that an interaction between at least one object of the at least two objects and a portion of the health information associated with the user comprises a personal health hazard to the user.

8. The mobile device of claim 7, wherein the health hazard warning comprises information about the interaction.

9. The mobile device of claim 8, wherein the health hazard warning comprises a severity interaction warning icon that identifies a severity of the personal health hazard, and wherein the severity interaction warning icon is arranged adjacent the first object and is arranged adjacent the second object while both of the at least two objects remain visible in the images.

10. The mobile device of claim 1, wherein the instructions further cause the processor to:
    determine, as part of determining the identity of the at least two objects, an identity of a first object of the at least two objects at a first time; and
    determine, as part of determining the identity of the at least two objects, an identity of a second object of the at least two objects at a second time subsequent to the first time, and
    wherein the interaction warning is presented by the display device only when the second object of the at least two objects appears in the images of the environment.

11. The mobile device of claim 1, wherein the instructions further cause the processor to output audio, via a speaker of the mobile device, comprising the information about each object when each object appears in the images of the environment.

12. The mobile device of claim 1, wherein the instructions further cause the processor to output a vibration, via a tactile transducer of the mobile device, upon determining the identity of the at least two objects in the environment.

13. A method, comprising:

receiving, from at least one camera of a mobile device, digital images of a medication and a food object, wherein the food object is a consumable other than the medication;

determining, based on the digital images received, an identity of the medication and of the food object;

retrieving, based on the identity, information about the medication and information about the food object;

determining an authentication of a user of the mobile device with a user health account;

presenting, by a display device of the mobile device when the user is determined to be unauthenticated with the user health account, the information about the food object while the food object remains visible in the digital images as the digital images are received from the at least one camera;

retrieving, from the user health account, health information for the user only when the user is determined to be authenticated with the user health account;

determining whether an interaction between the food object and a portion of the health information for the user comprises a health hazard to the user;

presenting, by the display device when the interaction between the food object and the portion of the health information for the user is determined to comprise the health hazard to the user, an interaction warning describing the interaction while the food object remains visible in the digital images, wherein the interaction warning is presented in a display location adjacent the food object; and presenting, by the display device when the portion of the health information comprises a known interaction between the medication and the food object, a health hazard warning when both the medication and the food object appear in the digital images at a same time, wherein the health hazard warning comprises a graphical icon linking the medication and the food object together.

14. The method of claim 13, wherein the interaction warning is presented as the digital images are received from the at least one camera.

15. The method of claim 14, wherein at least one of the information about the food object and the interaction warning are rendered via the display device as an augmented reality presentation, and wherein the at least one of the information about the food object and the interaction warning are overlaid upon the digital images received from the at least one camera, in real time, as the digital images are received from the at least one camera.

16. The method of claim 13, wherein the health information for the user comprises at least one medical treatment, prescribed medication, preexisting condition, and state of health of the user.

17. The method of claim 16, wherein the health information comprises a vision impairment as the preexisting condition, and wherein presenting the information about the food object while the food object remains visible in the digital images further comprises at least one of adjusting a contrast, a color, a filter of light, and a size of the information presented based on the vision impairment.

18. A non-transitory computer-readable medium comprising instructions stored therein that, when executed by a processor, cause the processor to:

receive, from a camera, video images of an environment;

determine, from the video images received, an identity of at least two objects in the environment, wherein a first object of the at least two objects corresponds to a medication and a vitamin and a second object of the at least two objects corresponds to a food;

retrieve, from a memory device based on the identity of the at least two objects in the environment, information about the at least two objects, wherein at least a portion of the information about the at least two objects is not visible on the at least two objects;

determine, based on the information about the at least two objects, that an interaction warning is associated with combining the at least two objects together;

present, by a display device as the video images of the environment are received and while the second object is present in the video images of the environment, the interaction warning adjacent the second object; and present, by the display device as the video images of the environment are received, a health hazard warning when both of the at least two objects appear in the video images of the environment at a same time, wherein the health hazard warning comprises a graphical icon linking both of the at least two objects together.

19. The non-transitory computer-readable medium of claim 18, wherein determining the identity of the at least two objects in the environment comprises at least one of visual recognition and optical character recognition of the at least two objects using artificial intelligence enabled by a machine learning engine analyzing the video images.

20. The non-transitory computer-readable medium of claim 18, wherein retrieving the information about the at least two objects comprises accessing a database comprising identities of objects and corresponding known interactions, ingredients, and names, and wherein the database comprises the identity of the at least two objects.

* * * * *